United States Patent
Dubois et al.

(10) Patent No.: US 8,852,886 B2
(45) Date of Patent: Oct. 7, 2014

(54) HOST CELLS AND METHODS OF PRODUCING DISULFIDE BOND CONTAINING PROTEINS

(75) Inventors: Jean-Yves Francois Dubois, Saint Beauzire (FR); Roelof Hendrik Matthijs Kouwen, Groningen (NL); Jan Maarten Van Dijl, Harkstede (NL)

(73) Assignee: Danisco US Inc., Palo Alto, CA (US)

( * ) Notice: Subject to any disclaimer, the term of this patent is extended or adjusted under 35 U.S.C. 154(b) by 518 days.

(21) Appl. No.: 12/934,631

(22) PCT Filed: Mar. 24, 2009

(86) PCT No.: PCT/IB2009/005368
§ 371 (c)(1),
(2), (4) Date: Mar. 2, 2011

(87) PCT Pub. No.: WO2009/118651
PCT Pub. Date: Oct. 1, 2009

(65) Prior Publication Data
US 2011/0236926 A1    Sep. 29, 2011

Related U.S. Application Data

(60) Provisional application No. 61/039,601, filed on Mar. 26, 2008, provisional application No. 61/039,611, filed on Mar. 26, 2008.

(51) Int. Cl.
*C12P 21/06* (2006.01)
*C12N 1/20* (2006.01)
*C12P 21/02* (2006.01)
*C12N 15/67* (2006.01)
*C12N 9/02* (2006.01)
*C12N 15/75* (2006.01)

(52) U.S. Cl.
CPC ......... *C12N 15/67* (2013.01); *C12Y 108/01009* (2013.01); *C12P 21/02* (2013.01); *C12Y 108/01008* (2013.01); *C12N 9/0036* (2013.01); *C12N 15/75* (2013.01)
USPC ..................................... 435/68.1; 435/252.1

(58) Field of Classification Search
CPC ........ C12P 21/02; C12N 15/00; C12N 15/70; C12N 15/75; C12N 2500/44; G01N 33/56944; A61K 39/092; C07K 14/315; C07K 14/195; C12Y 108/01008
See application file for complete search history.

(56) References Cited

U.S. PATENT DOCUMENTS 6,872,563 B1    3/2005 Beckwith et al.

FOREIGN PATENT DOCUMENTS

WO    WO-2004/056987 A1    7/2004

OTHER PUBLICATIONS

Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*

(Continued)

*Primary Examiner* — Alexander Kim
(74) *Attorney, Agent, or Firm* — Danisco US Inc.

(57) ABSTRACT

The invention provides for genetically modified *Bacillus* host cells having decreased cytoplasmic reductase activity, such as decreased TrxA activity, and a nucleic acid encoding a heterologous Staphylococcal oxidase. The invention also provides for methods of producing di-sulfide bond containing proteins using the host cells of the invention and methods of improving protein folding using the host cell of the invention.

16 Claims, 3 Drawing Sheets

(56) References Cited

OTHER PUBLICATIONS

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Mutation-rate (last viewed on May 30, 2012).*

Tam et al., The Intestinal Life Cycle of *Bacillus subtilis* and Close Relatives., Journal of Bacteriology, vol. 188, pp. 2692-2700, (2006).*

O32218 (last viewed on Dec. 17, 2012).*

Tanaka, T., et al., "Thioredoxin-2 (TRX-2) is an essential gene regulating mitochondria-dependent apoptosis." *The Embo Journal* 21(7): 1695-1703, 2002.

Anfinsen. "Principles That Govern the Folding of Protein Chains," *Science* 181:223-230, 1973.

Bolhuis et al. "Functional Analysis of Paralogous Thiol-disulfide Oxidoreductases in *Bacillus subtilis*," *J Biol Chem* 274:24531-24538, 1999.

Braun et al. "Improving Protein Secretion by Engineering Components of the Bacterial Translocation Machinery," *Curr Opin Biotechnol* 10:376-381, 1999.

Darmon et al. "A Disulfide Bond-Containing Alkaline Phosphatase Triggers a BdbC-Dependent Secretion Stress Response in *Bacillus subtilis*," *Appl Environ Microbiol* 72:6876-6885, 2006.

Dorenbos et al. "Thiol-disulfide Oxidoreductases are Essential for the Production of the Lantibiotic Sublancin 168," *J Biol Chem* 277:16682-16688, 2002.

Dumoulin et al. "*Staphylococcus aureus* DsbA is a Membrane-Bound Lipoprotein with Thiol-Sulfide Oxidoreductase Activity," *Archives of Microbiology* 184:117-128, 2005.

Inaba et al. "Crystal Structure of the DsbB-DsbA Complex Reveals a Mechanism of Disulfide Bond Generation," *Cell* 127:789-801, 2006.

International Search Report mailed Jul. 30, 2009 for PCT/IB2009/005368, 3 pp.

Kouwen et al. "Thiol-disulphide Oxidoreductase Modules in the Low-GC Gram-positive Bacteria," *Molecular Microbiol.* 64:984-999, 2007.

Kouwen et al. "Modulation of Thiol-Disulfide Oxidoreductases for Increased Production of Disulfide-Bond-Containing Proteins in *Bacillus subtilis*," Applied and Environmental Microbiology 74:7536-7545, 2008.

Meima et al. "The *bdbDC* Operon of *Bacillus subtilis* Encodes Thiol-disulfide Oxidoreductases required for Competence Development," *J Biol Chem* 277:6994-7001, 2002.

NCBI Accession No. NP390728, accessed at http://www.ncbi.nlm.nih.gov/protein/NP_390728, 2 pp, last viewed on Jul. 6, 2012.

Rietsch et al. "The Genetics of Disulfide Bond Metabolism," *Annu Rev Genet* 32:163-184, 1998.

Sarvas et al. "Post-translocational Folding of Secretory Proteins in Gram-positive Bacteria," *Biochim Biophys Acta* 1694:311-327, 2004.

Scharf et al. "Thioredoxin is an Essential Protein Induced by Multiple Stresses in *Bacillus subtilis*," *J Bacteriol* 180:1869-1877, 1998.

Smits et al. "Tricksy Business: Transcriptome Analysis Reveals the Involvement of Thioredoxin A in Redox Homeostasis, Oxidative Stress, Sulfur Metabolism, and Cellular Differentiation in *Bacillus subtilis*," *J Bacteriol* 187:3921-3930, 2005.

Sone et al. "Roles of Disulfide Bonds in Bacterial Alkaline Phosphatase," *J Biol Chem* 272:6174-6178, 1997.

Stein. "*Bacillus subtilis* antibiotics: structures, syntheses and specific functions," *Mol. Microbiol.* 56:845-857, 2005.

Westers et al. "*Bacillus subtilis* as Cell Factory for Pharmaceutical Proteins: A Biotechnological Approach to Optimize the Host Organism," *Biochim et Biophys Acta* 1694:299-310, 2004.

* cited by examiner

SEQUENCE LISTING

<160> NUMBER OF SEQ ID NOS: 14

<210> SEQ ID NO 1
<211> LENGTH: 354
<212> TYPE: DNA
<213> ORGANISM: Bacillus subtilis

<400> SEQUENCE: 1

```
gattcttaat cgcaagagcg ccggagcttc atgccggcgc tcttttcag gttttaaaac    60 agctccggca gggcatggta aagtacatga cagtgaagag gagatgtgat cttatgcttc   120
gtaccatttt aatgattatt ggggcaattg tagtgatcgg ggccattatc agatttgtgt   180
tttaaaaaaa gagcatatcc cattcaacca tataaaaatg agtaaaccgg ctgtgatcag   240
gaaaaaataa tttgtaagca ttaaaatagc gtgaacgaat gggagatgct atactaaaaa   300
tcatcatttc acattggagg aattcaataa tggctatcgt aaaagcaact gatc          354
```

<210> SEQ ID NO 2
<211> LENGTH: 104
<212> TYPE: PRT
<213> ORGANISM: Bacillus subtilis

<400> SEQUENCE: 2

```
Met Ala Ile Val Lys Ala Thr Asp Gln Ser Phe Ser Ala Glu Thr Ser
 1               5                  10                  15

Glu Gly Val Val Leu Ala Asp Phe Trp Ala Pro Trp Cys Gly Pro Cys
                20                  25                  30

Lys Met Ile Ala Pro Val Leu Glu Glu Leu Asp Gln Glu Met Gly Asp
            35                  40                  45

Lys Leu Lys Ile Val Lys Ile Asp Val Asp Glu Asn Gln Glu Thr Ala
        50                  55                  60

Gly Lys Tyr Gly Val Met Ser Ile Pro Thr Leu Leu Val Leu Lys Asp
 65                  70                  75                  80

Gly Glu Val Val Glu Thr Ser Val Gly Phe Lys Pro Lys Glu Ala Leu
                85                  90                  95

Gln Glu Leu Val Asn Lys His Leu
            100
```

<210> SEQ ID NO 3
<211> LENGTH: 600
<212> TYPE: DNA
<213> ORGANISM: Staphylococcus carnosus

<400> SEQUENCE: 3

```
atgaaaaaat tagcattatt agtttgcatt ggtattatcg ctgctgtatt acaaggatgt    60
tcacaaaaag accctgattt aaatagtaaa aatggaaaaa tcagagttgt agaatttgct   120
gattataaat gtccgtactg taaaaaagta gaagataata tcatgccgaa attagaaaaa   180
gattatattg ataaaggcaa agtggattat caaatggtta atgtggcttt tttaggtaaa   240
```

```
gattctatta ttggttcacg tgcaggtcat gcggtaaaaa atattgcacc taaacaatat      300
ttagattttc aaagaaaat ttttgctgta caacctgata cagaagacca taagaaacct      360
tggattaatg aaaaactgtt agacaagtta atcgatggat taaaaatctc taataaacaa     420
aaggcagata ttaaaaaaga ctataaaaca aaaaacagta atcttggaa agatgctgaa      480 aaagataaag catttgctaa aagaaaaat attgatactg tacctgtagt ttttgtggat      540
ggtaccaaat tggatgatcc gtatcatttt aaagaatata agatttact agaaaaataa      600
```

<210> SEQ ID NO 4
<211> LENGTH: 199
<212> TYPE: PRT
<213> ORGANISM: Staphylococcus carnosus

<400> SEQUENCE: 4

```
Met Lys Lys Leu Ala Leu Leu Val Cys Ile Gly Ile Ile Ala Ala Val
1               5                   10                  15

Leu Gln Gly Cys Ser Gln Lys Asp Pro Asp Leu Asn Ser Lys Asn Gly
            20                  25                  30

Lys Ile Arg Val Val Glu Phe Ala Asp Tyr Lys Cys Pro Tyr Cys Lys
        35                  40                  45

Lys Val Glu Asp Asn Ile Met Pro Lys Leu Glu Lys Asp Tyr Ile Asp
    50                  55                  60

Lys Gly Lys Val Asp Tyr Gln Met Val Asn Val Ala Phe Leu Gly Lys
65                  70                  75                  80

Asp Ser Ile Ile Gly Ser Arg Ala Gly His Ala Val Lys Asn Ile Ala
                85                  90                  95

Pro Lys Gln Tyr Leu Asp Phe Gln Lys Lys Ile Phe Ala Val Gln Pro
            100                 105                 110

Asp Thr Glu Asp His Lys Lys Pro Trp Ile Asn Glu Lys Leu Leu Asp
        115                 120                 125

Lys Leu Ile Asp Gly Leu Lys Ile Ser Asn Lys Gln Lys Ala Asp Ile
    130                 135                 140

Lys Lys Asp Tyr Lys Thr Lys Asn Ser Lys Ser Trp Lys Asp Ala Glu
145                 150                 155                 160

Lys Asp Lys Ala Phe Ala Lys Lys Asn Ile Asp Thr Val Pro Val
                165                 170                 175

Val Phe Val Asp Gly Thr Lys Leu Asp Asp Pro Tyr His Phe Lys Glu
            180                 185                 190

Tyr Lys Asp Leu Leu Glu Lys
        195
```

<210> SEQ ID NO 5
<211> LENGTH: 35
<212> TYPE: DNA
<213> ORGANISM: Artificial
<220> FEATURE:
<223> OTHER INFORMATION: synthetic primer

<400> SEQUENCE: 5

```
gggggactag taagaggagg agaaatatga gacaa                                35
```

<210> SEQ ID NO 6
<211> LENGTH: 33
<212> TYPE: DNA
<213> ORGANISM: Artificial
<220> FEATURE:
<223> OTHER INFORMATION: synthetic primer -continued

```
<400> SEQUENCE: 6
tttttgtgag catcccgtta aagcaaaggt cgc                                    33

<210> SEQ ID NO 7
<211> LENGTH: 33
<212> TYPE: DNA
<213> ORGANISM: Artificial
<220> FEATURE:
<223> OTHER INFORMATION: synthetic primer

<400> SEQUENCE: 7
ttaacgggat gctcacaaaa agaccctgat tta                                    33

<210> SEQ ID NO 8
<211> LENGTH: 40
<212> TYPE: DNA
<213> ORGANISM: Artificial
<220> FEATURE:
<223> OTHER INFORMATION: synthetic primer

<400> SEQUENCE: 8 ggggggatc cttatttttc tagtaaatct ttatattctt                              40

<210> SEQ ID NO 9
<211> LENGTH: 29
<212> TYPE: DNA
<213> ORGANISM: Artificial
<220> FEATURE:
<223> OTHER INFORMATION: synthetic primer

<400> SEQUENCE: 9
ggggaattca taagacagcc gatgtggtc                                         29

<210> SEQ ID NO 10
<211> LENGTH: 29
<212> TYPE: DNA
<213> ORGANISM: Artificial
<220> FEATURE:
<223> OTHER INFORMATION: synthetic primer

<400> SEQUENCE: 10
gggggatccg tagaatagct cggcgaatg                                         29

<210> SEQ ID NO 11
<211> LENGTH: 29
<212> TYPE: DNA
<213> ORGANISM: Artificial
<220> FEATURE:
<223> OTHER INFORMATION: synthetic primer

<400> SEQUENCE: 11
gggggatccc ggcaaagtaa gtcttgagg                                         29

<210> SEQ ID NO 12
<211> LENGTH: 29
<212> TYPE: DNA
<213> ORGANISM: Artificial
<220> FEATURE:
<223> OTHER INFORMATION: synthetic primer

<400> SEQUENCE: 12
ggggtcgaca ttgttctaac cgcaagcgc                                         29

<210> SEQ ID NO 13
```

```
<211> LENGTH: 29
<212> TYPE: DNA
<213> ORGANISM: Artificial
<220> FEATURE:
<223> OTHER INFORMATION: synthetic primer

<400> SEQUENCE: 13
gggggtaccc attgccgtgt tccactgtt                                    29

<210> SEQ ID NO 14
<211> LENGTH: 29
<212> TYPE: DNA
<213> ORGANISM: Artificial
<220> FEATURE:
<223> OTHER INFORMATION: synthetic primer

<400> SEQUENCE: 14
gggctgcagg gcaaccgtat cctctttga                                    29
```

HOST CELLS AND METHODS OF PRODUCING DISULFIDE BOND CONTAINING PROTEINS

This application claims priority under 35 USC §371 to PCT/IB2009/005368 (WO 2009/118651), with an international filing date of 24 Mar. 2009, which claims priority to U.S. 61/039,601, filed 28 Mar. 2008, and U.S. 61/039,611, filed 28 Mar. 2008.

FIELD OF INVENTION

The invention provides for genetically modified *Bacillus* host cells having decreased cytoplasmic reductase activity, such as decreased TrxA activity, and a nucleic acid encoding a heterologous oxidase, such as a Staphylococcal oxidase. The invention also provides for methods of producing disulfide bond containing proteins using the host cells of the invention and methods of improving folding of such disulfide bond containing proteins using the host cell of the invention.

BACKGROUND

Disulfide bonds are pivotal for the correct folding, structural integrity and activity of numerous proteins found in nature. Without the correct oxidation that links their cysteines into disulfide bonds, these proteins will neither be fully stable nor biologically active. Importantly, many eukaryotic proteins of biopharmaceutical interest contain multiple disulfide bonds. Among others, these include human insulin, insulin like growth factor, human growth hormone, brain-derived neutrophic factor, nerve growth factor, lipases, Bowman-Birk protease inhibitor, and antibody fragments.

The formation of disulfide bonds can occur spontaneously, but this process is very slow and non-specific. For this reason, enzymes have evolved that catalyze the formation (oxidation) of disulfide bonds in vivo. These enzymes belong to the class of thiol-disulfide oxidoreductases (TDORs). This class of enzymes also contains enzymes that break (reduce) or isomerise disulfide bonds. Cytoplasmic TDORs generally function as reductases while their extracytoplasmic equivalents are oxidases or isomerases (Dorenbos et al., (2005) p. 237-269. In S. G. Pandalai (ed.), *Recent Res. Devel. Microbiology* 9. Research Signpost, Kerala, India; Ritz et al., *Annu. Rev. Microbiol.* 55:21-48, 2001; Tan et al., *Chembiochem.* 5:1479-1487, 2004). The enzyme-dependent formation of disulfide bonds is, in fact, a prime reason why proteins containing such bonds are still troublesome to produce in large amounts using bacterial cell factories. Slow and/or non-specific oxidation of overproduced proteins in bacterial cell factories may result in slow and/or incorrect folding of these proteins, making them vulnerable to proteolytic degradation and potentially rendering them inactive unless they are further processed in vitro into correctly folded and active product.

Previous studies on disulfide bond formation in *Bacillus subtilis* have shown that this organism contains at least four TDORs with presumed oxidase activity. These proteins were named Bdb (*Bacillus* disulfide bond) proteins, and annotated as BdbA-D. The bdbA and bdbB genes are located within the SPβ prophage region, and are therefore only present in the sequenced *B. subtilis* strain 168. Biological functions have been identified for BdbB, BdbC and BdbD, but not for BdbA. The Bdb function was found to be modular in the sense that different Bdb proteins can cooperate to perform different functions (Kouwen et al., *Mol. Microbiol.* 64:984-999). The integral membrane protein BdbB shares a high degree of sequence similarity with BdbC and both are of major importance for folding of the secreted SPβ-encoded lantibiotic sublancin 168, which contains two disulfide bonds (Bolhuis, et al., *J. Biol. Chem.* 274:24531-24538, 1999, Dorenbos et al., *J. Biol. Chem.* 277:16682-16688, 2002, Stein, *Mol. Microbiol.* 56:845-857, 2005). On the contrary, BdbC together with BdbD are of major importance for the biogenesis of the pseudopilin ComGC, while BdbB is dispensable for this process (Meima, *J. Biol. Chem.* 277:6994-7001, 2002). ComGC is an important element of the DNA-uptake machinery of *B. subtilis* and, consistent with its TDOR requirement for folding into a protease-resistant conformation, it contains an essential intra-molecular disulfide bond (Chung et al., *Mol. Microbiol.* 29:905-913, 1998). BdbC and BdbD are also required for folding of a secreted heterologous protein by *B. subtilis*, namely the alkaline phosphatase PhoA of *E. coli* (Bolhuis et al., *J. Biol. Chem.* 274:24531-24538, 1999; Darmon et al., *Appl. Environ. Microbiol.* 72:6876-6885, 2006, Kouwen et al., *Mol. Microbiol.* 64:984-999. 2007, Meima et al., *J. Biol. Chem.* 277:6994-7001, 2002). This TDOR requirement relates to the fact that *E. coli* PhoA contains two disulfide bonds that are indispensable both for the enzymatic activity and stability of this protein (Sone et al., *J. Biol. Chem.* 272:6174-6178, 1997). Taken together, these previous observations indicate that the combined BdbA-D proteins provide the basic machinery for the folding of both homologous and heterologous disulfide bond-containing proteins in *B. subtilis*.

*Bacillus* organisms also contain thioredoxins, which are small, heat stable, ubiquitous TDORs that are involved in a large variety of processes, ranging from enzyme activation to mitochondria-dependent apoptosis (Tanaka et al., *EMBO J.* 21:1695-1703, 2002). During catalysis, the cysteine residues of their CxxC active site undergo a reversible oxidation-reduction reaction. In the bacterial cytoplasm, thioredoxin is usually present in a reduced state in order to prevent the formation of disulfide bonds in cytoplasmic proteins.

It has been reported that BdbC and BdbD cooperate as a redox pair in an oxidation pathway of *B. subtilis* (Sarvas et al., *Biochim. Biophys. Acta* 1694:311-327, 2004). It was therefore proposed that BdbD functions as the major oxidase for secreted cysteine-containing proteins, thereby facilitating the formation of disulfide bonds. Subsequently, the reduced BdbD would be re-oxidized by the quinone reductase homologue BdbC. To become re-oxidized for a next catalytic reaction, BdbC would then donate its electrons to quinones in the electron transport chain. This system resembles the DsbA and DsbB redox pair of *E. coli* (Inaba et al. *Cell* 127:789-801, 2006), Regeimbal et al. *J. Biol. Chem.* 277:32706-32713, 2002), Rietsch & Beckwith. *Annu. Rev. Genet.* 32:163-184, 1998). Despite the presence of four Bdb proteins, the total oxidative power of *B. subtilis* is rather limited. In an attempt to increase the thiol-oxidizing capacity, overexpression of individual or combinations of Bdb proteins has been attempted. However, this did not result in significantly improved production of proteins with disulfide bonds (Darmon et al., *Appl. Environ. Microbiol.* 72:6876-6885, 2006, Dorenbos et al., *J. Biol. Chem.* 277:16682-16688, 2002, Meima et al., *J. Biol. Chem.* 277:6994-7001, 2002).

There have been other reports that host cells, such as bacteria, exhibit relatively poor performance in the production of proteins with disulfide bonds (Braun et al., Curr. Opin. Biotechnol. 10:376-381, 1999; Anfinsen, Science 181:223-230, 1973; Westers et al., Biochim. Biophys. Acta 1694:299-310, 2004).

SUMMARY OF INVENTION

The present invention relates generally to strategies that increase the thiol-oxidizing power of host cells, such as *B. subtilis*.

In addition to increasing the levels of an oxidase in a host cell, the invention provides for host cells having decreased levels of those TDORs with reductase activity, such as thioredoxins (e.g. the major cytoplasmic disulfide bond reductase TrxA). The data presented herein demonstrates that this reduction in thioredoxin activity results in increased yields of secreted *E. coli* PhoA, a disulfide bond containing protein, while having no effect on yield of proteins that do not contain disulfide bonds. Furthermore, the yields of disulfide bond containing protein may be improved by introduction of a nucleic acid encoding a staphylococcal DsbA polypeptide, which is known as one of the strongest bacterial thiol oxidases (Dumoulin et al., *Arch. Microbiol.* 184:117-128, 2005). The invention further provides for an improvement in yield of disulfide bond containing protein achieved by adding redox-active compounds to the growth medium of these host cells.

The data described herein illustrate the development of methods for improved production of disulfide bond-containing proteins in *Bacillus*. The improved production can be achieved by: (1) depletion of a TrxA polypeptide in the *Bacillus* host cell; and/or (2) co-expressing in the *Bacillus* host cell a staphylococcal thiol oxidase (e.g., a DsbA polypeptide) with the disulfide bond-containing protein that is to be produced; and/or (3) using growth medium supplemented with a redox-active compound, such as cysteine; and (4) a combination of these three approaches. Proof-of-principle was obtained by the combined utilization of these three approaches for the optimized secretion of the disulfide bond-containing protein PhoA from *E. coli*. This resulted in about 3.5-fold increased amounts of active PhoA protein in the growth medium.

The data presented herein demonstrates that coexpression of the strong oxidase DsbA of *S. aureus* with *E. coli* PhoA had been shown to result in increased active PhoA secretion. In particular, coexpression with the DsbA proteins of either *S. aureus* or *S. carnosus* in *B. subtilis* resulted in higher levels of active extracellular PhoA protein. Furthermore, coexpression of in particular *S. carnosus* DsbA resulted in lowered PhoA degradation and increased accumulation of pro-PhoA processing intermediates. This indicates that the presence of staphylococcal DsbA proteins facilitates a more efficient folding of PhoA, most likely through improved thiol oxidation. In this respect, DsbA from *S. aureus* and *S. carnosus* appear to be equally effective, but use of the *S. carnosus* DsbA has the obvious advantage that it comes from a food-grade organism that has the GRAS status, like *B. subtilis*. Therefore, DsbA from a nondisease-causing *staphylococcus* is a preferred thiol oxidase for improvement of *Bacillus* cell factories in biotechnological applications.

The invention provides for genetically modified host cells, such as *Bacillus* host cells, that are useful for the production of disulfide bond containing proteins, wherein the host cells (i) have a genetic modification to decrease or deplete the activity or cellular expression of a cytoplasmic reductase in the host cell, and/or (ii) comprise a nucleic acid encoding a heterologous oxidase, such as a staphylococcal oxidase or mutant thereof that retains oxidase activity. Such genetically modified host cells can be further modified to comprise a nucleic acid encoding a heterologous disulfide bond containing protein. The genetically modified host cells of the invention may be of any type. However, a preferred host cell is a *Bacillus* host cell, such as *Bacillus subtilis, Bacillus amyloliquefaciens, Bacillus licheniformis, Bacillus brevis, Bacillus alcalophilus, Bacillus pumilus, Bacillus clausii, Bacillus cereus, Bacillus thuringiensis,* or *Bacillus alodurans*. In one embodiment, the host cell is *Bacillus subtilis*. The genetically modified host cells comprise a genetic modification that decreases the activity of a cytoplasmic reductase. This genetic modification may be a deletion mutation, substitution mutation or insertion mutation in the gene encoding the cytoplasmic reductase or in an expression control region, e.g. promoter. The invention also provides for host cells wherein the genetic modification is an insertion of an inducible promoter to control gene expression. In some embodiments, the decrease in cytoplasmic reductase activity is the result of the decrease in the expression of (i.e., depletion of) the cytoplasmic reductase polypeptide, while in other embodiments the decrease in activity is the result of expression of inactive cytoplasmic reductase polypeptide, or the result of increased degradation of the cytoplasmic reductase, or the result of increased expression of an inhibitor of the cytoplasmic reductase. The cytoplasmic reductase may be any cytoplasmic reductase active in the host cell. In exemplary embodiments, the cytoplasmic reductase is a thiol-disulfide reductase such as TrxA, TrxC, YbdE, YdbP, YdfQ, YkuV, YosR YtpP, YusE, BdbA, ResA, StoA, SpoIVH or YneN. In another embodiment, the cytoplasmic reductase is gluatredoxin such as GrxA, GrxB or GrxC or glutathione oxidoreductase such as Gor. In some embodiments, the cytoplasmic reductase of the host cell with decreased activity is a TrxA polypeptide, including homologs from other bacteria or mutants that retain reductase activity. The TrxA polypeptide may comprise an amino acid sequence selected from the group consisting of an amino acid sequence of SEQ ID NO:2 or any of the amino acid sequences listed in Table 1, an amino acid sequence encoded by the nucleic acid sequence of SEQ ID NO:1 or any of the nucleic acid sequences listed in Table 1, an amino acid sequence that is at least about 60%, 65%, 70%, 75%, 80%, 85%, 90%, 95%, 98% or 99% identical to the amino acid sequence of SEQ ID NO:2 or any of the amino acid sequences listed in Table 1, an amino acid sequence encoded by a nucleic acid sequence that is at least about 60%, 65%, 70%, 75%, 80%, 85%, 90%, 95%, 98% or 99% identical to the nucleic acid sequence of SEQ ID NO:1 or any of the nucleic acid sequences listed in Table 1, and an amino acid sequence encoded by a nucleic acid sequence that hybridizes under stringent conditions to the complement of SEQ ID NO:1. In some embodiments, the genetically modified host cells express a heterologous oxidase that is a staphylococcal oxidase. Preferably the staphylococcal oxidase is from a nondisease-causing *Staphylococcus* bacterium, for example, *Staphylococcus carnosus*. The nucleic acid sequence encoding the heterologous oxidase may be a plasmid or expression vector that is introduced into the host cell via transformation, transfection or infection. In some embodiments, the heterologous oxidase is a staphylococcal DsbA polypeptide, including homologs from other bacteria or mutants that retain reductase activity. The DsbA polypeptide may comprise an amino acid sequence selected from the group consisting of an amino acid sequence of SEQ ID NO:4, or any of the amino acid sequences listed in Table 2, an amino acid sequence encoded by the nucleic acid sequence of SEQ ID NO:3 or any of the nucleic acid sequences listed in Table 2, an amino acid sequence that is at least about 60%, 65%, 70%, 75%, 80%, 85%, 90%, 95%, 98% or 99% identical to the amino acid sequence of SEQ ID NO:4 or any of the amino acid sequences listed in Table 2, an amino acid sequence encoded by a nucleic acid sequence that is at least about 60%, 65%, 70%, 75%, 80%, 85%, 90%, 95%, 98% or 99% identical to the nucleic acid sequence of SEQ ID NO:3 or any of the nucleic acid sequences listed in Table 2, and an amino acid sequence encoded by a nucleic acid sequence that hybridizes under stringent conditions to the complement of SEQ ID NO:3.

The invention also provides for cultures of the genetically modified host cells described above. In one embodiment, the culture is grown in a medium containing a redox-active compound. In exemplary embodiments, redox-active compound is selected from the group consisting of cysteine, cystine, glutathione, 2-mercaptoethanol (BME), 1,4-dithiothreitol (DTT), thiosulfate, dithionite, metabisulfite, sulfite, N-ethylmaleimide or mycothiol.

The invention also provides for a genetically modified *Bacillus* host cell e.g. *Bacillus subtilis*, comprising a genetic modification to decrease activity of a TrxA polypeptide in the host cell, wherein the TrxA polypeptide comprises the amino acid sequence of SEQ ID NO:2, and a nucleic acid sequence encoding a heterologous nondisease-causing staphylococcal DsbA polypeptide, wherein the DsbA polypeptide comprises the amino acid sequence of SEQ ID NO:4.

The invention also provides for methods of producing a disulfide bond containing protein comprising growing any of the genetically modified host cells of the invention described above in media containing a redox-active compound, wherein the genetically modified host cell produces the disulfide bond containing protein and secretes the protein into the media, and optionally isolating such disulfide bond containing protein from the media. In illustrative embodiments, the redox-active compound is selected from the group consisting of cysteine, cystine, glutathione, 2-mercaptoethanol (BME), 1,4-dithiothreitol (DTT), thiosulfate, dithionite, metabisulfite, sulfite, N-ethylmaleimide or mycothiol. In some embodiments, the host cell does not secrete the protein and the protein is isolated from the cells.

The invention also provides for methods of producing a disulfide bond containing protein in a *Bacillus* host cell e.g., a *Bacillus subtilis* host cell, comprising genetically modifying the host cell to decrease activity of a cytoplasmic reductase in the host cell, introducing a nucleic acid sequence encoding a heterologous staphylococcal oxidase or mutant thereof that retains oxidase activity in the host cell, wherein the oxidase is from a nondisease-causing *Staphylococcus* bacterium, and growing the host cell in media containing a redox-active compound, wherein the host cell produces the disulfide bond containing protein and secretes the protein into the media. These methods may be carried out with any of the host cells of the invention. In some embodiments, the host cell does not secrete the protein and the protein is isolated from the cells. In some embodiments, the activity of a cytoplasmic reductase that is reduced in the genetically modified host cell is the activity of a TrxA cytoplasmic reductase, including homologs from other bacteria or mutants that retain reductase activity. The TrxA polypeptide may comprise an amino acid sequence selected from the group consisting of an amino acid sequence of SEQ ID NO:2 or any of the amino acid sequences listed in Table 1, an amino acid sequence encoded by the nucleic acid sequence of SEQ ID NO:1 or any of the nucleic acid sequences listed in Table 1, an amino acid sequence that is at least about 60%, 65%, 70%, 75%, 80%, 85%, 90%, 95%, 98% or 99% identical to the amino acid sequence of SEQ ID NO:2 or any of the amino acid sequences listed in Table 1, an amino acid sequence encoded by a nucleic acid sequence that is at least about 60%, 65%, 70%, 75%, 80%, 85%, 90%, 95%, 98% or 99% identical to the nucleic acid sequence of SEQ ID NO:1 or any of the nucleic acid sequences listed in Table 1, and an amino acid sequence encoded by a nucleic acid sequence that hybridizes under stringent conditions to the complement of SEQ ID NO:1. Decreased cytoplasmic reductase activity is caused by mutation in the cytoplasmic reductase gene. For example, a deletion mutation, a substitution mutation and an insertion mutation are examples of mutations that are made in the cytoplasmic reductase gene to decrease the reductase activity. In some embodiments, the decreased reductase activity is controlled by an inducible promoter. In some embodiments, the heterologous staphylococcal oxidase, or mutant thereof that retains oxidase activity, is introduced into the host cell by transforming the host cell with a plasmid comprising a gene encoding the oxidase. Preferably the staphylococcal oxidase is from a nondisease-causing *Staphylococcus* bacterium, for example, *Staphylococcus carnosus*. The oxidase may be any oxidase such as BdbA, DsbA, DsbB, DsbC, DsbD, DipZ, DsbE, CcmG, DsbG, BdbB, BdbC or BdbD. In some embodiments, the heterologous oxidase is a staphylococcal DsbA polypeptide, including homologs from other bacteria or mutants that retain reductase activity. The DsbA polypeptide may comprise an amino acid sequence selected from the group consisting of an amino acid sequence of SEQ ID NO:4, or any of the amino acid sequences listed in Table 2, an amino acid sequence encoded by the nucleic acid sequence of SEQ ID NO:3 or any of the nucleic acid sequences listed in Table 2, an amino acid sequence that is at least about 60%, 65%, 70%, 75%, 80%, 85%, 90%, 95%, 98% or 99% identical to the amino acid sequence of SEQ ID NO:4 or any of the amino acid sequences listed in Table 2, an amino acid sequence encoded by a nucleic acid sequence that is at least about 60%, 65%, 70%, 75%, 80%, 85%, 90%, 95%, 98% or 99% identical to the nucleic acid sequence of SEQ ID NO:3 or any of the nucleic acid sequences listed in Table 2, and an amino acid sequence encoded by a nucleic acid sequence that hybridizes under stringent conditions to the complement of SEQ ID NO:3. The aforementioned method may be carried out wherein the host cells are grown in media containing a redox-active compound. In illustrative embodiments, the redox-active compound is selected from the group consisting of cysteine, cystine, glutathione, 2-mercaptoethanol (BME), 1,4-dithiothreitol (DTT), thiosulfate, dithionite, metabisulfite, sulfite, N-ethylmaleimide or mycothiol. In one embodiment, the invention provides for methods of producing a disulfide bond containing protein in a genetically modified *Bacillus* host cell that exhibits (a) decreased expression of a TrxA polypeptide in the host cell, wherein the TrxA polypeptide comprises the amino acid sequence of SEQ ID NO:2, and/or (b) increased expression of a heterologous staphylococcal DsbA polypeptide in the host cell, wherein the DsbA polypeptide comprises the amino acid sequence of SEQ ID NO:4, such methods comprising growing the host cell in media containing a redox-active compound, and optionally isolating the disulfide bond containing protein from the media, wherein the host cell produces the disulfide bond containing protein and secretes the protein into the media. Such methods include methods of improving folding of a recombinant protein, or improving yield of active recombinant protein, for example, at least about 2-fold, 3-fold, 4-fold, 5-fold, or higher yields. In some embodiments, the host cell does not secrete the protein and the protein is isolated from the cells.

The invention also provides for a method of improving folding of a recombinant protein, or improving yield of active recombinant protein. Such a method may comprise a method as described above, wherein the active recombinant protein is a disulfide bond containing protein and the genetically modified *Bacillus* host cell (for example as described hereinbefore) is grown under conditions that permit expression of and improve proper folding of a disulfide bond containing protein. The protein may then optionally be isolated from the media. A method of this aspect may comprise growing a genetically modified *Bacillus* host cell, e.g., a *Bacillus subti-* lis host cell, in media containing a redox-active compound, under conditions that permit expression of and improve yield of an active disulfide bond containing protein, wherein said host cell (i) exhibits decreased cytoplasmic reductase activity and/or (ii) exhibits increased expression of a heterologous staphylococcal oxidase, or mutant thereof that retains oxidase activity, and/or (iii) secretes a heterologous disulfide bond containing protein; and optionally, isolating said protein from the media. This method may be carried out with any of the host cells of the invention. Improvements in proper protein folding can be determined by detecting higher yields (e.g., higher mg active protein/liter of cell culture or higher activity of recombinant protein per liter of cell culture) of active recombinant disulfide bond containing protein, for example, at least about 2-fold, 3-fold, 4-fold, 5-fold, or higher yields, relative to the yield from unmodified host cells in media that has not been supplemented with redox-active compounds. In some embodiments, the cytoplasmic reductase of the host cell with decreased activity is a TrxA polypeptide, including homologs from other bacteria or mutants that retain reductase activity. The TrxA polypeptide may comprise an amino acid sequence selected from the group consisting of an amino acid sequence of SEQ ID NO:2 or any of the amino acid sequences listed in Table 1, an amino acid sequence encoded by the nucleic acid sequence of SEQ ID NO:1 or any of the nucleic acid sequences listed in Table 1, an amino acid sequence that is at least about 60%, 65%, 70%, 75%, 80%, 85%, 90%, 95%, 98% or 99% identical to the amino acid sequence of SEQ ID NO:2 or any of the amino acid sequences listed in Table 1, an amino acid sequence encoded by a nucleic acid sequence that is at least about 60%, 65%, 70%, 75%, 80%, 85%, 90%, 95%, 98% or 99% identical to the nucleic acid sequence of SEQ ID NO:1 or any of the nucleic acid sequences listed in Table 1, and an amino acid sequence encoded by a nucleic acid sequence that hybridizes under stringent conditions to the complement of SEQ ID NO:1. Decreased cytoplasmic reductase activity is caused by mutation in the cytoplasmic reductase gene. For example, a deletion mutation, a substitution mutation and an insertion mutation are examples of mutations that are made in the cytoplasmic reductase gene to decrease the reductase activity. In some embodiments, the decreased reductase activity is controlled by an inducible promoter. In some embodiments, the heterologous staphylococcal oxidase, or mutant thereof that retains oxidase activity, is introduced into the host cell by transforming the host cell with a plasmid comprising a gene encoding the oxidase. Preferably the staphylococcal oxidase is from a nondisease-causing *Staphylococcus* bacterium, for example, *Staphylococcus carnosus*. The oxidase may be any oxidase such as BdbA, DsbA, DsbB, DsbC, DsbD, DipZ, DsbE, CcmG, DsbG, BdbB, BdbC or BdbD. In some embodiments, the heterologous oxidase is a staphylococcal DsbA polypeptide, including homologs from other bacteria or mutants that retain reductase activity. The DsbA polypeptide may comprise an amino acid sequence selected from the group consisting of an amino acid sequence of SEQ ID NO:4, or any of the amino acid sequences listed in Table 2, an amino acid sequence encoded by the nucleic acid sequence of SEQ ID NO:3 or any of the nucleic acid sequences listed in Table 2, an amino acid sequence that is at least about 60%, 65%, 70%, 75%, 80%, 85%, 90%, 95%, 98% or 99% identical to the amino acid sequence of SEQ ID NO:4 or any of the amino acid sequences listed in Table 2, an amino acid sequence encoded by a nucleic acid sequence that is at least about 60%, 65%, 70%, 75%, 80%, 85%, 90%, 95%, 98% or 99% identical to the nucleic acid sequence of SEQ ID NO:3 or any of the nucleic acid sequences listed in Table 2, and an amino acid sequence encoded by a nucleic acid sequence that hybridizes under stringent conditions to the complement of SEQ ID NO:3. The aforementioned method may be carried out wherein the host cells are grown in media containing a redox-active compound. In illustrative embodiments, the redox-active compound is selected from the group consisting of cysteine, cystine, glutathione, 2-mercaptoethanol (BME), 1,4-dithiothreitol (DTT), thiosulfate, dithionite, metabisulfite, sulfite, N-ethylmaleimide or mycothiol.

DETAILED DESCRIPTION

Figure 1:
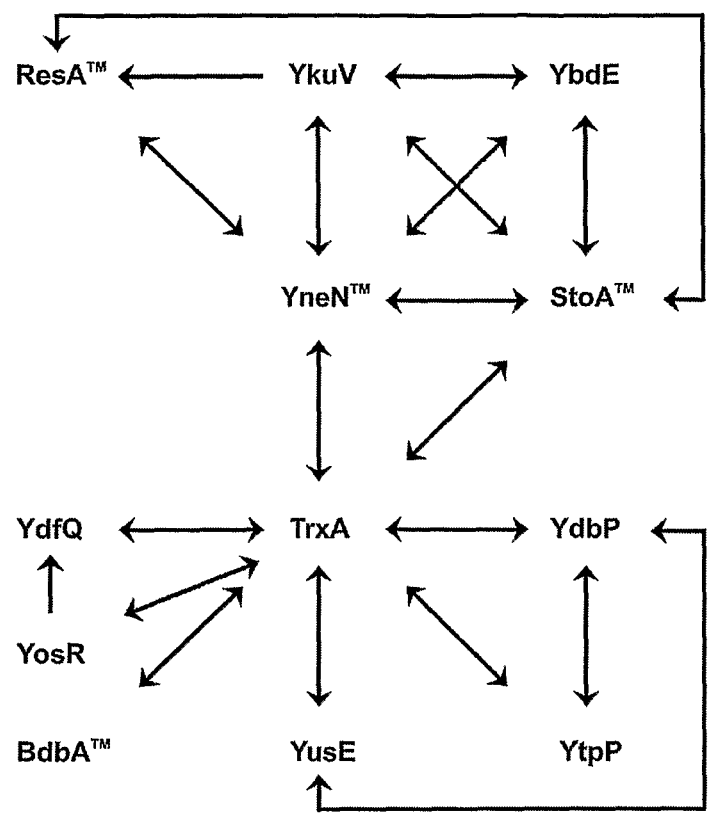
FIG. 1 depicts the sequence relationships between thioredoxin-like proteins of *B. subtilis*. Arrows between proteins indicate a positive identification by BlastP of the protein to which the arrow points using the other protein as a query sequence. Proteins with a transmembrane (TM) segment are indicated.

The present invention provides genetically modified host cells and methods of using these host cells for production of disulfide bond containing proteins and for improving folding of recombinant proteins. The host cells of the invention comprise genetic modifications to decrease the activity of a cytoplasmic reductase and to express a heterologous oxidase polypeptide. The host cells of the invention may further comprise a heterologous disulfide bond containing protein. The invention further provides for improved methods of producing active disulfide bond containing protein achieved by adding redox-active compounds to the growth medium of the host cells.

In previous studies, the roles of membrane-associated TDORs in the secretion of *E. coli* PhoA were investigated and this analysis demonstrated that BdbC and BdbD were important for preventing the degradation of PhoA that was translocated across the membrane (Bolhuis et al., *J. Biol. Chem.* 274:24531-24538, 1999; Meima, et al., *J. Biol. Chem.* 277:6994-7001, 2002). These studies also revealed that, despite the PhoA folding activity of BdbCD, substantial amounts of translocated PhoA were degraded (Darmon et al. *Appl. Environ. Microbiol.* 72:6876-6885, 2006; Kouwen et al., *Mol. Microbiol.* 64:984-999, 2007). This was likely to be due to the known limited capacity for disulfide bond formation of *B. subtilis* (Sarvas et al., *Biochim. Biophys. Acta* 1694:311-327, 2004). At the time cytoplasmic TDORs was not included in the studies, because these are generally believed to function as thiol reductases rather than as thiol oxidases that might facilitate the folding of PhoA. The data described herein demonstrate how the thiol oxidizing power of *B. subtilis* could be increased. Lowering the cellular levels of the cytoplasmic TDORs would decrease the thiol-reductive power and concomitantly increase the oxidative power. Remarkably, of the ten thioredoxin-like proteins of *B. subtilis* tested, only one significantly impacted the secretion of PhoA. This was the essential thioredoxin TrxA. However, this data cannot rule out a role of other thioredoxin-like proteins in the present invention. The data provided herein indicates that TrxA counteracts the production of secreted active PhoA, most likely due to its general thiol reductase function in the cytoplasm.

The data described herein demonstrates that depletion of TrxA in *B. subtilis* resulted in about 1.5 to 2-fold increased extracellular levels of *E. coli* PhoA. This effect of TrxA depletion appears to be specific for the disulfide bond containing protein PhoA, because the secretion of AmyQ, which contains no disulfide bonds, and all other secreted *B. subtilis* proteins that can be detected by 1D or 2D PAGE were not affected under these conditions. (See Example 2) In fact, the increased PhoA levels coincided with the disappearance of PhoA degradation products and the appearance of incompletely processed pro-PhoA in the medium. This indicates that PhoA folding was improved upon TrxA depletion. The results of previous DNA array analyses showed that the expression of none of the known genes for major secretion machinery components or proteases of *B. subtilis* is affected by TrxA depletion (Smits et al., *J. Bacteria* 187:3921-3930, 2005). Taken together, these findings indicate that TrxA influences the activity (but not the amounts) of secretion machinery components that are specifically involved in PhoA secretion. Indeed, TrxA was shown to have a significant impact on the redox state of the extracytoplasmic thiol-disulfide oxidoreductase BdbD since TrxA depletion resulted in increased cellular levels of oxidized BdbD molecules. These observations indicate that a diminished reductive power of the cytoplasm, as a consequence of TrxA depletion, results in increased levels of oxidized BdbD molecules. Thus, TrxA depletion has the opposite effect of a bdbC mutation, which results in strongly reduced folding of PhoA (Bolhuis et al., *J. Biol. Chem.* 274:24531-24538, 1999) and, at the same time, significantly increased levels of reduced BdbD. Notably, the improved PhoA secretion by TrxA-depleted cells still depends on the presence of BdbC. Therefore, it seems that the increased levels of oxidized BdbD molecules in TrxA depleted cells increase the cellular capacity to oxidize exported proteins, such as PhoA. As PhoA contains two disulfide bonds, while disulfide bonds are absent from AmyQ and most known secreted proteins of *B. subtilis*, the data indicates that the improved secretion of PhoA by TrxA-depleted cells can be attributed to improved post-translocational disulfide bond formation in PhoA rather than improved pre-PhoA translocation across the membrane.

The invention provides for genetically modified host cells comprising a genetic modification that decreases or suppresses the activity of a cytoplasmic reductase in the host cell, relative to the activity of such cytoplasmic reductase in the corresponding unmodified host cell. This invention may be carried out by decreasing or suppressing the activity of any cytoplasmic reductase in a host cell. Decreased activity may be detected by decreased expression of the cytoplasmic reductase, as illustrated herein, or by decreased activity of the cytoplasmic reductase, as illustrated herein.

The term "reductase" refers to an enzyme that reduces molecules in its environment. A reductase acts by donating electrons, thereby becoming more oxidized upon reducing a substrate. In a some embodiments, the cytoplasmic reductase is a thiol-disulfide reductase, thioredoxin or a thioredoxin-like protein such as TrxA, TrxC, YbdE, YdbP, YdfQ, YkuV, YosR, YtpP, YusE, BdbA, ResA, StaA, SpoIVH or YneN or the equivalent protein in a particular host cell. In another embodiment, the cytoplasmic reductase is a gluatredoxin such as GrxA, GrxB or GrxC or glutathione oxidoreductase such as Gor or the equivalent protein in a particular host cell.

In some embodiments, the cytoplasmic reductase is a *Bacillus* TrxA protein such as those proteins listed in Table 1 or homologs from other prokaryotic or eukaryotic cells or mutants thereof that retain reductase activity.

In some embodiments, the cytoplasmic reductase is a *B. subtilis* TrxA polypeptide having the amino acid sequence set out as Genbank Accession No. P14949 (MAIVKATDQSFSA-ETSEGVVLADFWAPWCGPCKMIAPV-LEELDQEMGDKLKIV KIDVDENQETAGKYGVM-SIPTLLVLKDGEVVETSVGFKPKEALQELVNKHL; SEQ ID NO:2) or having an amino acid sequence encoded by the nucleic acid sequence set out as Genbank Accession No. X99275 (GATTCTTAATCGCAAGAGCGCCGGAGCT-TCATGCCGGCGCTCTTTTTCAGGTT TTAAAA-CAGCTCCGGCAGGGCATGGTAAAGTA-CATGACAGTGAAGAGGAGAT GTGATCTTATGCTTCGTACCATTTTAAT-GATTATTGGGGCAATTGTAGTGATCG GGGCCATTAT-CAGATTTGTGTTTTAAAAAAAGAG-CATATCCCATTCAACCATA TAAAAATGAGTAAACCGGCTGTGATCAG-GAAAAAATAATTTGTAAGCATTAA AATAGCGT-GAACGAATGGGAGATGCTATAC-TAAAAATCATCATTTCACATTGG AGGAATTCAATAATGGCTATCGTAAAAG-CAACTGATC; SEQ ID NO:1). Other homologs can be identified by identifying homologous polypeptides in Genbank or, e.g., by using SEQ ID NO:3 as a hybridization probe to identify homologous nucleic acids in host cell nucleic acid libraries. Mutants can be produced by making mutations (insertions, deletions or substitutions) in the sequence of a known TrxA. In some embodiments conservative substitutions are made, e.g. outside of the catalytic region. Mutants that are about 60%, 65%, 70%, 75%, 80%, 85%, 90%, 95%, 98% or 99% identical are contemplated.

TABLE 1

| Species | DNA Genbank Accession No. | Protein Genbank Accession No. |
|---|---|---|
| *Bacillus subtilis* | X99275<br>SEQ ID NO: 1 | P14949<br>SEQ ID NO: 2 |
| *Bacillus amyloliquefaciens* FZB42 | NC_009725.1<br>(2676451 ... 2676765 complement) | YP_001422145.1 |
| *Bacillus licheniformis* ATCC 14580 | NC_006322.1<br>(2880210 ... 2880524, complement) | YP_092558.1 |
| *Bacillus cereus* E33L | NC_006274.1<br>(4378394 ... 4378708, complement) | YP_085847.1 |
| *Bacillus licheniformis* ATCC 14580 | NC_006270.3<br>(2880357 ... 2880671, complement) | YP_082264.1 |
| *Bacillus thuringiensis* serovar *konkukian* str. 97-27 | NC_005957.1<br>(777956 ... 778375, complement) | YP_035016.1 |
| *Bacillus subtilis* subsp. *subtilis* str. 168 | NC_000964.2<br>(2912092 ... 2912406, complement) | NP_390728 |
| *Bacillus thuringiensis* str. Al Hakam | NC_008600.1<br>(4319019 ... 4319333, complement) | YP_896824.1 |
| *Bacillus thuringiensis* serovar *konkukian* str. 97-27 | NC_005957.1<br>(4319019 ... 4319333, complement) | YP_038572.1 |
| *Bacillus clausii* KSM-K16 | NC_006582.1<br>(2798565 ... 2798879, complement) | YP_176164.1 |

TABLE 1-continued

| Species | DNA Genbank Accession No. | Protein Genbank Accession No. |
|---|---|---|
| Bacillus pumilus SAFR-032 | NC_009848.1 (2517212 ... 2517526, complement) | YP_001487729.1 |
| Bacillus halodurans C-125 | NC_002570.2 (3213709 ... 3214023, complement) | NP_243964.1 |

The invention also provides for genetically modified host cells comprising a nucleic acid sequence encoding a heterologous oxidase. The term "oxidase" refers to an enzyme that oxidizes molecules in its environment. An oxidase acts by accepting electrons, thereby becoming more reduced upon oxidizing a substrate. The term "heterologous" refers to a protein that is not produced in the host cell under normal (unmodified) or wild type conditions such as the parent host cell. A heterologous oxidase may be from any species or strain that is different from the host cell. Alternatively, a heterologous oxidase may be from the same species or strain of the host cell but is expressed by a nucleic acid sequence that has been introduced into the host cell. In exemplary embodiments, the heterologous oxidase will be a Staphylococcal oxidase. In some embodiments, the heterologous oxidase will be a Staphylococcal oxidase from a nondisease-causing Staphylococcus bacterium such as Staphylococcus carnosus or Staphylococcus xylosus.

In some embodiments, the oxidase is BdbA, DsbA, DsbB, DsbC, DsbD, DipZ, DsbE, CcmG, DsbG, BdbB, BdbC, BdbD. In one embodiment, the oxidase is a Staphylococcal DsbA protein or a Staphylococcal DsbA-like protein such as those proteins listed in Table 2, or homologs from other prokaryotic or eukaryotic cells or mutants thereof that retain oxidase activity.

In some embodiments, the oxidase is a S. carnosus DsbA having the amino acid sequence of set out as SEQ ID NO:4 (MKKLALLVCIGIIAAVLQGCSQKDPDLN-SKNGKIRVVEFADYKCPYCKKVEDNI MPKLEKDYID-KGKVDYQMVNVAFLGKDSIIG-SRAGHAVKNIAPKQYLDFQKKIF AVQPDTEDHKKPWINEKLLDKLIDG-LKISNKQKADIKKDYKTKNSKSWKDAEKD KAF-AKKKNIDTVPVVFVDGTKLDDPYHFKEYKDLLEK; SEQ ID NO:4) or having an amino acid sequence encoded by the nucleic acid sequence set out as SEQ ID NO:3 (AT-GAAAAAATTAGCATTATTAGTTTGCAT-TGGTATTATCGCTGCTGTATTACA AGGATGTTCA-CAAAAAGACCCTGATTTAAATAGTAAAAATGGAA-AAATCAGA GTTGTAGAATTTGCTGATTATAAATGTC-CGTACTGTAAAAAAGTAGAAGATAA TATCATGC-CGAAATTAGAAAAAGATTATAT-TGATAAAGGCAAAGTGGATTATC AAATGGTTAATGTGGCTTTTTTAGG-TAAAGATTCTATTATTGGTTCACGTGCAG GTCAT-GCGGTAAAAAATATTGCACCTAAA-CAATATTTAGATTTCAAAAGAAA ATTTTTGCTGTACAACCTGATACAGAA-GACCATAAGAAACCTTGGATTAATGA AAAACTGT-TAGACAAGTTAATCGATGGAT-TAAAAATCTCTAATAAACAAAAG GCAGATATTAAAAAAGACTATAAAA-CAAAAAACAGTAAATCTTGGAAAGATG CTGAAAAAGATAAAGCATTTGCTAAAAA-GAAAAATATTGATACTGTACCTGTA GTTTTTGTG-GATGGTACCAAATTGGATGATCCGTAT-CATTTTAAAGAATATAA AGATTTACTAGAAAAATAA; SEQ ID NO:3) or a mutant thereof that retains oxidase activity.

Other homologs can be identified by identifying homologous polypeptides in Genbank or, e.g., by using SEQ ID NO:3 as a hybridization probe to identify homologous nucleic acids in host cell nucleic acid libraries. Mutants can be produced by making mutations (insertions, deletions or substitutions) in the sequence of a known oxidase. In some embodiments conservative substitutions are made, e.g. outside of the catalytic region. Mutants that are about 60%, 65%, 70%, 75%, 80%, 85%, 90%, 95%, 98% or 99% identical are contemplated.

TABLE 2

| Species | DNA Genbank Accession No. | Protein Genbank Accession No. |
|---|---|---|
| Staphylococcus aureus subsp. aureus str. Newman | NC_009641.1 (2535803 ... 2536402, complement) | YP_001333342.1 |
| Staphylococcus aureus | AF321274 475 ... 1074, complement | AAG41993 |
| Staphylococcus epidermidis RP62A | NC_002976.3: (2017873 ... 2018469; complement) | YP_189555 |
| Staphylococcus epidermidis RP62A | CP000029.1 (2017873 ... 2018469; complement) | AAW52799 |
| Staphylococcus epidermidis ATCC 12228 | NC_004461.1: (2024437 ... 2025033; complement) | NP_765542 |
| Staphylococcus epidermidis ATCC 12228 | AE015929.1 (2024437 ... 2025033; complement) | AAO05628.1 |
| Staphylococcus aureus subsp. aureus USA300_TCH1516 | NZ_AASB01000185.1 (8229 ... 8828; complement) | ZP_02761363.1 |

It is important to note that a single enzyme may exhibit both reducing activity and oxidizing activity depending on the cellular condition. Therefore, a protein that acts as a reductase under some conditions may act as an oxidase under different conditions.

The cytoplasmic reductase polynucleotide or the oxidase polynucleotides of the invention also include nucleotide sequences that are substantially equivalent to the polynucleotides recited above. Polynucleotides according to the invention can have, e.g., at least about 65%, at least about 70%, at least about 75%, at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99% sequence identity to a nucleic acid sequence recited herein, wherein the polynucleotides encode polypeptides having reductase activity or oxidase activity accordingly.

The cytoplasmic reductase or the oxidase polynucleotides of the invention include nucleic acid sequence fragments that hybridize under stringent conditions to the nucleotide sequences recited herein, or complements thereof, which fragment is greater than about 5 nucleotides, or 7 nucleotides, or greater than 9 nucleotides or greater than 17 nucleotides. Fragments of, e.g. 15, 17, or 20 nucleotides or more that are selective for (i.e., specifically hybridize to any one of the polynucleotides of the invention) are contemplated.

The term "stringent" is used to refer to conditions that are commonly understood in the art as stringent. Stringent conditions can include highly stringent conditions (i.e., hybridization to filter-bound DNA under in 0.5 M NaHPO$_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.). In instances wherein hybridization of deoxyoligonucleotides is concerned, additional exemplary stringent hybridization conditions include washing in 6×SSC/0.05% sodium pyrophosphate at 37° C. (for 14-base oligos), 48° C. (for 17-base oligos), 55° C. (for 20-base oligos), and 60° C. (for 23-base oligos).

The sequences falling within the scope of the present invention are not limited to these specific sequences, but also include mutants thereof that retain the desired biological activity. The term "mutant" includes allelic and species variants, homologs from other eukaryotic or prokaryotic cells, and substantial equivalents. Allelic and species variants can be routinely determined by comparing the sequence provided above, a representative fragment thereof, or a nucleotide sequence at least 90% identical, or 95% identical, to the sequence recited above with a sequence from another isolate of the same species. Furthermore, to accommodate codon variability, the invention includes nucleic acid molecules coding for the same amino acid sequences as do the specific open reading frames (ORF) disclosed herein. In other words, in the coding region of an ORF, substitution of one codon for another codon that encodes the same amino acid is expressly contemplated.

Species and host cell strain homologs (or orthologs), of the disclosed polynucleotides and proteins are also provided by the present invention. Species or strain homologs may be isolated and identified by making suitable probes or primers from the sequences provided herein and screening a suitable nucleic acid source from the desired species.

The reductase and oxidase polypeptides of the invention include, but are not limited to, a polypeptide comprising: the amino acid sequences set forth above or an amino acid sequence encoded by the nucleotide sequences set forth above, or the corresponding full length or mature protein. The invention also provides biologically active variants of the amino acid sequences set forth above or the corresponding full length or mature protein; and "substantial equivalents" thereof (e.g., with at least about 65%, at least about 70%, at least about 75%, at least about 80%, at least about 85%, 86%, 87%, 88%, 89%, at least about 90%, 91%, 92%, 93%, 94%, typically at least about 95%, 96%, 97%, more typically at least about 98%, or most typically at least about 99% amino acid identity) that retain biological activity. Polypeptides encoded by allelic variants may have a similar, increased, or decreased activity compared to polypeptides set out above.

Host Cells

The invention provides for genetically modified host cells and methods thereof for production of disulfide bond containing proteins. The term "host cell" is used to refer to a cell which has been transformed, transfected or infected or is capable of being transformed, transfected or infected with a nucleic acid sequence and then of expressing a selected gene of interest to recombinantly produce a protein of interest. The term includes the progeny of the parent cell, whether or not the progeny is identical in morphology or in genetic make-up to the original parent, so long as the selected gene or genetic modification is present.

The invention may be carried out with any host organism which is capable of expressing heterologous polypeptides, and is capable of being genetically modified. A host organism is preferably a unicellular host organism, however, multicellular organisms are also encompassed by the invention, provided the organism can be modified as described herein and a polypeptide of interest expressed therein. For purposes of clarity, the term "host cell" will be used herein throughout, but it should be understood, that a host organism can be substituted for the host cell, unless unfeasible for technical reasons.

In some embodiments the host cell is a prokaryotic cell, such as a bacterial cell. The host cell may be a gram positive bacterial cells, such as *Bacillus* or gram negative bacteria such as *E. coli*. The host organisms may be aerobic or anaerobic organisms. In some embodiments, host cells are those which have characteristics which are favorable for expressing polypeptides, such as host cells having fewer proteases than other types of cells. Suitable bacteria for this purpose include archaebacteria and eubacteria, for example, Enterobacteriaceae. Other examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla,* and *Paracoccus*. Additional examples of useful bacteria include *Corynebacterium, Lactococcus, Lactobacillus,* and *Streptomyces* species, in particular *Corynebacterium glutamicum, Lactococcus lactis, Lactobacillus plantarum, Streptomyces coelicolor, Streptomyces lividans*. Suitable *E. coli* hosts include *E. coli* DHB4, *E. coli* BL-21 (which are deficient in both lon (Phillips et al. *J. Bacteriol.* 159: 283, 1984) and ompT proteases), *E. coli* AD494, *E. coli* W3110 (ATCC 27,325), *E. coli* 294 (ATCC 31,446), *E. coli* B, and *E. coli* X1776 (ATCC 31,537). Other strains include *E. coli* B834 which are methionine deficient and, therefore, enables high specific activity labeling of target proteins with $^{35}$S-methionine or selenomethionine (Leahy et al. *Science* 258: 987, 1992). Yet other strains of interest include the BLR strain, and the K-12 strains HMS174 and NovaBlue, which are recA-derivative that improve plasmid monomer yields and may help stabilize target plasmids containing repetitive sequences.

Suitable *Bacillus* strains include *Bacillus subtilis, Bacillus anzyloliguelaciens, Bacillus licheniformis, Bacillus brevis, Bacillus alcalophilus, Bacillus clauseii, Bacillus cereus, Bacillus pumilus, Bacillus thuringiensis,* or *Bacillus halodurans*. The Gram-positive bacterium *B. subtilis* is a preferred organism for secretory protein production in the biotechnological industry. Its popularity is primarily based on the fact that *B. subtilis* lacks an outer membrane, which retains many proteins in the periplasm of Gram-negative bacteria such as *Escherichia coli*. Accordingly, the majority of *B. subtilis* proteins that are transported across the cytoplasmic membrane end up directly in the growth medium. Additionally, the lack of an outer membrane implies that proteins produced with *B. subtilis* are free from lipopolysaccharide (endotoxin). Other advantages of using *B. subtilis* as a protein production host are its high genetic amenability, the availability of strains with mutations in nearly all of the ~4100 genes, a toolbox with strains and vectors for gene expression, and the fact that this bacterium is generally recognized as safe (Braun et al., *Curr. Opin. Biotechnol.* 10:376-381, 1999; Kobayashi et al., *Proc. Natl. Acad. Sci. U.S.A* 100:4678-4683, 2003; Kunst et al. *Nature* 390:249-256, 1997; Zeigler et al., In E. Goldman and L. Green (ed.), *Practical Handbook of Microbiology*. CRC Press, Boca Raton, Fla., 2008).

In another embodiment, the host cell is a eukaryotic cell, such as a yeast cell or a mammalian cell. Examples of mammalian cells include, but are not limited to Chinese hamster ovary cells (CHO) (ATCC No. CCL61), CHO DHFR-cells (Urlaub et al., *Proc. Natl. Acad. Sci. USA,* 97:4216-4220 (1980)), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available to those skilled in the art of protein expression.

Many strains of yeast cells known to those skilled in the art are also available as host cells for the expression of the polypeptides of the present invention. Exemplary yeast cells include, for example, *Saccharomyces cerivisae* and *Pichia pastoris*. Fungi, such as *Aspergillum*, are also available as host cells for the expression of the polypeptides of the present invention.

Additionally, where desired, insect cell systems may be utilized in the methods of the present invention. Such systems are described for example in Kitts et al., *Biotechniques*, 14:810-817 (1993); Lucklow, *Curr. Opin. Biotechnol.*, 4:564-572 (1993); and Lucklow et al. (*J. Virol.*, 67:4566-4579 (1993). Exemplary insect cells are Sf-9 and Hi5 (Invitrogen, Carlsbad, Calif.).

The invention also provides for cultures of the genetically modified host cells of the invention. A "culture" of host cells is a colony or growth of the host cells carried out in a nutrient medium including selective or differential media. The term "culture" includes primary cells and their progeny and cultures derived therefrom without regard for the number of transfers. It is also understood that all progeny of host cells may not be precisely identical in DNA content, due to deliberate or inadvertent mutations. Mutant progeny that have the same function or biological activity as screened for in the originally transformed cell are included.

The nutrient medium may be a solid or semi-solid agar or a liquid medium. An exemplary nutrient media include Luria Bertani (LB) media, blood agar, chocolate agar, Thayer-Martin agar (TM), Bile Esculin Agar (BEA), Cysteine Lactose Electrolyte Deficient agar (CLED), Hektoen Enteric (HE), MacConkey agar (MAC), Mannitol Salt Agar (MSA), Mueller Hinton agar, Önöz agar, Phenylethyl Alcohol Agar (PEA), and Xylose-Lysine-Deoxycholate agar (XLD). Generally, a culture of host cells is grown in an incubator using standard techniques in the art, e.g. as described in Sambrook et al., (1989). *Molecular Cloning: A Laboratory Manual*, 2nd edition. Cold Spring Harbor Laboratory, Cold Spring Harbor, N.Y. and Ausubel et al., eds., *Current Protocols in Molecular Biology*, Green Publishers Inc. and Wiley and Sons, NY (1994).

The cultures of the invention may be grown and may produce the recombinant protein in shaker flasks, as described, e.g., in Qui et al. (1998) *Appl. Environ. Microbiol.* 64:4891. Alternatively, the cultures of the invention may be grown and may produce the recombinant protein in a fermentator, as described, e.g., in Qui et al. Id.

Genetic Modifications

The invention provides for genetically modified host cells that have decreased activity of a cytoplasmic reductase. The term "decreased activity" refers to reduction or depletion or complete elimination of reductase activity within the cytoplasm of a host. The decreased activity would be determined as compared to the activity in a corresponding wild type or unmodified host cell such as a unmodified *Bacillus* host cell. The decreased cytoplasmic reductase activity may be accomplished by decreased expression of the reductase polypeptide, decreased transcription of the gene encoding the cytoplasmic reductase amino acid sequence, reducing or inhibiting translation of the RNA encoding the reductase amino acid sequence, or inactivation or inhibition of the cytoplasmic reductase polypeptide. The decrease in reductase activity may be carried out directly by reducing or depleting the activity of a particular reductase or indirectly by altering the reductase pathway upstream or downstream from a particular reductase. Guidance to measure the reductase activity of the genetically modified host cell is provided in the assays described herein such as assays in with the cell extract is labeling with 4-acetamido-4'-maleimidyl-stilbene-2,2'-disulfonate (AMS) as described in Example 2 herein.

Reduction or depletion of endogenous reductase activity of a host cell can be achieved by the functional deletion or inactivation of a gene encoding the reductase. In one embodiment, a plasmid can be used that integrates into the chromosome of a host cell at a specific site of the chromosome, thereby disrupting the cytoplasmic reductase gene. In another embodiment, at least one mutation is introduced into the reductase coding sequence such that the activity of reductase is modulated, for example a point mutation is introduced which inactivates the activity. These mutation or disruptions in the cytoplasmic reductase gene may be insertion, deletion or substitution mutations. The mutation may be created by inserting using site directed mutagenesis, PCR amplification, or other appropriate methods, where the primer(s) have the desired point mutations (see Sambrook et al., supra, and Ausubel et al., supra, for descriptions of mutagenesis techniques).

Modification in a nucleic acid sequence may result in conservative and/or non-conservative modifications of the amino acid sequence relative to the naturally occurring or wild type sequence. Conservative modifications to the amino acid sequence will produce variant or mutant polypeptides having functional and chemical characteristics similar to those of naturally occurring polypeptide. In contrast, substantial modifications in the functional and/or chemical characteristics of polypeptides may be accomplished by selecting substitutions in the amino acid sequence, that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those of skill in the art that nucleic acid and polypeptide molecules described herein may be chemically synthesized as well as produced by recombinant means.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the polypeptide that are homologous with non-human IL-17 receptor like polypeptide orthologs, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.,* 157:105-131 (1982). It is known that certain amino acids may be substituted for other amino acids having a similar hydropathic index or score and still retain a similar biological activity. In making changes based upon the hydropathic index, the substitution of amino acids whose hydropathic indices are within is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the polypeptide.

Exemplary amino acid substitutions are set forth in the following Table 3.

TABLE 3

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of a polypeptide using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a polypeptide to such similar polypeptides. With such a comparison, one can identify residues and portions of the molecules that are conserved among similar polypeptides. It will be appreciated that changes in areas of a polypeptide that are not conserved relative to such similar polypeptides would be less likely to adversely affect the biological activity and/or structure of a polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a polypeptide that correspond to amino acid residues that are important for activity or structure in similar polypeptides. One skilled in the art can also analyze the three-dimensional structure and amino acid sequence in relation to that structure in similar polypeptides. In view of that information, one skilled in the art may predict the alignment of amino acid residues of an IL-17 receptor like polypeptide with respect to its three dimensional structure. Numerous scientific publications have been devoted to the prediction of secondary structure, and to the identification of epitopes, from analyses of amino acid sequences. See Chou et al., Biochemistry, 13(2):222-245, 1974; Chou et al., *Biochemistry*, 113(2):211-222, 1974; Chou et al., *Adv. Enzymol. Relat. Areas Mol. Biol.*, 47:45-148, 1978; Chou et al., *Ann. Rev. Biochem.*, 47:251-276 and Chou et al., *Biophys. J.*, 26:367-384, 1979. Moreover, computer programs are currently available to assist with predicting antigenic portions and epitopic core regions of proteins. Examples include those programs based upon the. Examples include those programs based upon the Jameson-Wolf analysis (Jameson et al., *Comput. Appl. Biosci.*, 4(1):181-186, 1998 and Wolf et al., *Comput. Appl. Biosci.*, 4(1):187-191, 1988), the program PepPlot® (Brutlag et al., *CABS*, 6:237-245, 1990), and Weinberger et al., *Science*, 228:740-742, 1985), and other new programs for protein tertiary structure prediction (Fetrow et al., *Biotechnology*, 11:479-483, 1993).

Transcription and translation can be inhibited by introducing into, or expressing, antisense nucleic acids in the host cell. Alternatively, these processes can be inhibited by contacting the host cells with small organic molecules which interfere with these processes. In addition, the expression of a reductase in a host cell can also be reduced or eliminated by modulating the expression of one or more proteins that control the expression of the reductase in the host cell by acting upstream of the reductase gene in its regulation. For example, expression of a reductase can be decreased by reducing the expression or activity of a factor that is necessary for the expression of the reductase. Alternatively, reductase expression can be reduced or eliminated by the use of constructs that allow for the expression or activation of a protease that degrades the reductase. This can be carried out, e.g., by inserting a protease sensitive site in the reductase (see, e.g., Ehrman et al. *Proc. Natl. Acad. Sci. USA* 94:13111, 1997).

In a further embodiment, a reduction or elimination of reductase activity in a host cell may be carried out using an inducible promoter which allows for said activity to be switched on or off in the host cell at a desired moment. Moreover, said activity can be induced or repressed in a reversible manner. The invention provides a host cell with an inducible reductase activity. In some embodiments, a host cell with inducible reductase activity is obtained by first deleting endogenous reductase activity of said host cell and subsequently providing the host cell with a recombinant nucleic acid encoding a reductase protein that is operationally linked to an inducible promoter sequence. "Inducible" promoters are promoters which direct transcription at an increased or decreased rate upon binding of a transcription factor or an inducer. The synthesis or the promoter binding ability of a transcription factor within the host cell can be controlled by exposing the host to an "inducer" or removing an inducer from the host cell medium. Accordingly, to regulate expression of an inducible promoter, an inducer is added or removed from the growth medium of the host cell.

An "inducer" is a chemical or physical agent which, when given to a population of cells, will increase the amount of transcription from specific genes. These are usually small molecules whose effects are specific to particular operons or groups of genes, and can include sugars, phosphate, alcohol, metal ions, hormones, heat, cold, and the like. A commonly used inducer is isopropylthiogalactoside (IPTG) because it is nonmetabolizable inducer. As is exemplified herein (see Example 2) particularly suitable promoter sequence comprises an IPTG inducible promoter sequence, such as PSPAC. Additional exemplary inducible promoters are an arabinose promoter in which the nucleic acid is only expressed in the presence of L-arabinose, the tacII promoter which is induced by lactose, the pho gene promoter which is induced by low phosphate concentration in the medium, UV-sensitive inducible promoters, temperature sensitive inducible promoters and antibiotic inducible promoters to name a few. A conditional trxA mutant host cell strain (ItrxA) was constructed by placing this essential gene under the transcriptional control of the IPTG-dependent PSPAC promoter of a plasmid.

In yet another embodiment, a method or a host cell according to the invention comprises a host cell in which reductase activity is modulated via a repressible system. The primary difference between repressible and inducible systems is the result that occurs when an effector molecule binds to the repressor. With inducible systems, the binding of the effector molecule, i.e. an inducer, to the repressor greatly reduces the affinity of the repressor for the operator, the repressor is released and transcription proceeds. The lac operon is an example of an inducible system. With repressible systems, the binding of the effector molecule to the repressor greatly increases the affinity of repressor for the operator and the repressor binds and stops transcription. Thus, for the trp operon, the addition of tryptophan (the effector molecule) to the host cell environment shuts off the system because the repressors binds at the operator.

In a further embodiment, the host cell may express a ortholog or a homolog of a heterologous oxidase polypeptide in which the variant (ortholog or homolog) retain the desired oxidase activity. Guidance for determining whether the variants retain the desired oxidase activity are described herein.

Method of identifying amino acid sequences that are identical to the polypeptide of interest are known in the art. Some methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., *Nucl. Acid Res.*, 12:387, 1984); Genetics Computer Group, University of Wisconsin, Madison, Wis.), BLASTP, BLASTN, and FASTA (Altschul et al. *J. Mol. Biol.*, 215:403-410, 1990). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al., *Atlas of Protein Sequence and Structure*, vol. 5, supp.3 (1978) for the PAM 250 comparison matrix; Henikoff et al., *Proc. Natl. Acad. Sci. USA,* 89:10915-10919, 1992 for the BLOSUM 62 comparison matrix) is also used by the algorithm.

Assays for Measuring Reductase and Oxidase Activity

In order to determine if the genetically modified host cells has decreased, reduced or depleted reductase activity, relative to the activity of such reductase in the corresponding unmodified host cell, the modified and unmodified host cells may be subjected to an assay to measure the relative amount of reductase expressed or the relative activity as measured by reduction of an appropriate substrate. Relative amounts of reductase enzyme expressed may be measured, e.g., by Western blot, Western blot analysis, SDS-polyacrylamide gel electrophoresis, non-denaturing gel electrophoresis, high performance liquid chromatography (HPLC) separation, immunoprecipitation, and/or activity assays such as DNA binding gel shift assays and alkaline phosphatase assay.

The substrate of the redox reaction assay is dependent upon the particular enzyme being analyzed, and a skilled artisan will understand which substrate is appropriate for the assay. For example, substrates for the cytoplasmic reductaseTrxA are AccB, AhpC, AhpF, ArsC, CysH, MsrA, NrdEF, PdhD, OdhB, Spx, YdfQ, and a substrate for the oxidase DsbA is *E. coli* PhoA.

In one exemplary assay, the redox state of the purified proteins, or proteins in complex samples such as cell extracts, may be monitored by labeling with 4-acetamido-4'-maleimidyl-stilbene-2,2'-disulfonate (AMS), prior to separation by SDS-PAGE under non-reducing conditions. AMS only binds covalently to free thiol groups in reduced protein molecules, thereby giving the reduced proteins a higher mass than the oxidized ones and a method of measuring the rate of reductase. The quantity of AMS labeling may be measured using standard techniques in the art such as using protein 50 assay chips on a 2100 Bioanalyzer (Agilent Technologies).

In addition, the redox potential of a protein, which is a measure of whether a protein is more reducing or oxidizing, can be determined by various methods, such as by calculation from the equilibrium constant of the redox reaction involving a reference with known redox potential using the Nernst equation. The commonly used references are defined glutathione/glutathione disulfide (GSH/GSSG) buffers or NADPH/NADP+ coupled via an appropriate reductase (Gilbert *Adv. Enzymol. Relat. Areas Mol. Biol.* 63:69, 1990). Another method is set forth in Krause et al. *J. Biol. Chem.* 299: 9494, 1991. One method for determining redox potentials of proteins, e.g., members of thioredoxin superfamily and variants thereof, is described in Aslund et al. *J. Biol. Chem.* 272: 30780, 1997 and in Mossner et al. *Prot. Sci.* 7:1233, 1998. Briefly, this method of pair-wise equilibration described in Aslund et al. for obtaining $E^{o'}$ is based on accurate determinations of the equilibrium constant, $K_{12}$ for the reversible thiol-disulfide exchange reaction between various pairs of redox active proteins. Standard state redox potentials are then obtained through equilibration with known standards, e.g., either Trx"PDI" or Trx, whose redox potential has been determined independently (Krause et al. *J. Biol. Chem.* 266:9494, 1991) via coupling to NADPH ($E^{o'}=-315$ mV).

In certain cases, the redox potential of a protein is linked to its pKa value. For example, in the case of DsbA, a linear correlation between redox potential and the pKa value of the nucleophilic thiol of the active site has been demonstrated (Krause et al. *J. Biol. Chem.* 266:9494, 1991). A major function of the active site motif (CX1X2C) is to modulate the pKa value of the nucleophilic thiol and thereby the stability of the reduced form of the protein relative to the oxidized form. Thus, in the case of DsbA, the very low pKa value of 3.5 (Nelson et al. *Biochemistry* 33:5974, 1994) is an important factor for its highly oxidizing properties. Accordingly, the identification of a protein, e.g., a thioredoxin variant or mutant, having oxidizing properties may be identified by the selection of a variant having a low pKa value. The pKa can be determined by methods known in the art, and described, e.g., in Nelson et al., supra.

Additional assays that measure the reducing activity of an enzyme include the beta-hydroxyethylene disulfide (HED) reduction assay as described in Holmgren et al. (*J. Biol. Chem.* 254, 3664, 1979), spectrophotometrically monitoring of in vitro reduction of insulin disulfides as described in Luthman and Holmgren *J. Biol. Chem.* 257:6686, 1979 and Moessner et al. *J. Biol. Chem.* 274: 25254, 1999. In addition, the reducing capacity of an enzyme may be measured in a Ribonucleotide Reductase Activity, as described in Thelander et al., *Methods Enzymol.* 51: 227, 1978, and Holmgren *J. Biol. Chem.* 254: 9113, 1979, by monitoring the conversion of [$^3$H]CDP to [$^3$H]dCDP by 10 μg of ribonucleotide reductase. Other substrates that can be used for determining the reducing capacity of an enzyme include lipoic acid and oxidized DTT as described in Moessner et al., *J. Biol. Chem.* 274: 25254, 1999.

Assays for assessing disulfide bond isomerization in vitro are standard in the art. One exemplary assay is measuring the ability of the enzyme to isomerize a misoxidized form of bovine pancreatic trypsin inhibitor (BPTI) as described in Zapun et al. *Biochemistry* 34: 5075, 1995. Additional assays for determining the ability of an enzyme to catalyze the formation of disulfide bonds are described in Zapun and Creighton *Biochemistry* 33: 5202, 1994, and Jonda et al. *EMBO J.* 18: 3271, 1999. Generally, an enzyme and a reduced substrate are incubated together and the amount of reduced and oxidized substrates is determined, e.g., by HPLC or Mass Spectrometry. Exemplary substrates include ribonuclease or hirudin.

Production of Recombinant Disulfide Bond Containing Proteins

The invention provides for method of producing disulfide bond containing proteins by growing the genetically modified host cells of the invention wherein the host cell secretes the protein into the culture media. The term "disulfide bond formation" refers to the process of forming a covalent bond between two cysteines present in one or two polypeptides. Oxidation of disulfide bonds is mediated by thiol-disulfide exchange between the active site cysteines of enzymes and cysteines in the target protein. Disulfide bond formation is catalyzed by enzymes which are referred to as catalysts of disulfide bond formation.

The genetically modified host cell may comprise a nucleic acid sequence encoding a disulfide bond containing protein. The invention contemplates production of any disulfide bond containing protein, including but not limited to human insulin, insulin like growth factor, human growth hormone, brain-derived neutrophic factor, nerve growth factor, lipases, Bowman-Birk protease inhibitor, and antibody fragments. Recombinant expression techniques conducted in accordance with the descriptions set forth below may be followed to produce disulfide bond containing proteins. For example, by inserting a nucleic acid sequence which encodes the amino acid sequence of a disulfide bond containing proteins into an appropriate vector, one skilled in the art can readily produce large quantities of the desired nucleotide sequence. Alternatively, a polynucleotide encoding the amino acid sequence of a disulfide bond containing proteins can be inserted into an expression vector. By introducing the expression vector into a genetically modified host cell of the invention, the encoded disulfide bond containing proteins may be produced in large amounts.

A nucleic acid molecule encoding the amino acid sequence of disulfide bond containing proteins may be inserted into an appropriate expression vector using standard ligation techniques. For a review of expression vectors, see *Meth. Enz., v.* 185, D. V. Goeddel, ed. Academic Press Inc., San Diego, Calif. (1990). The vector or nucleic acid is inserted into the genetically modified host cell using standard methods of transformation, transfection or infection. "Transfection" refers to the taking up of an expression vector by a host cell whether or not any coding sequences are in fact expressed. Exemplary transfection methods include $CaCl_2$ and electroporation. "Transformation" refers to introducing DNA into an organism so that the DNA is replicable, either as an extrachromosomal element or by chromosomal integrant. Depending on the host cell used, transformation is done using standard techniques appropriate to such cells. Exemplary transformation method include electroporation and calcium treatment employing calcium chloride is generally used for bacterial cells that contain substantial cell-wall barriers. Another exemplary transformation utilizes polyethylene glycol/DMSO, as described in Chung and Miller, *Nucleic Acids Res.,* 16: 3580, 1988.

The vector is typically selected to be functional in the particular host cell employed (i.e., the vector is compatible with the host cell machinery such that amplification of the gene and/or expression of the gene can occur). One type of vector is a plasmid. In general, plasmid vectors contain replicon and control sequences that are derived from species compatible with the host cell. The vector ordinarily carries a replication site, as well as marker sequences that are capable of providing phenotypic selection in transformed cells. Exemplary plasmids pBR322, a plasmid derived from an *E. coli* species (see, e.g., Bolivar et al., *Gene,* 2: 95, 1977), pBR322 contains genes for ampicillin and tetracycline resistance, pBR322 plasmid, or other microbial plasmid or phage. Alternatively, the plasmid may be modified to contain, promoters that can be used by the microbial organism for expression of the selectable marker genes.

In some embodiments, the culture media contains a redox-active compound. The term "redox" refers to oxidation/reduction reactions, which are chemical reactions in which a molecule has its oxidation state changed. The term "redox-active compound" is a compound susceptible or able to be reduced or oxidized. Exemplary redox-active compounds include cysteine, cystine, cytamine, glutathione (GSH), dithiobios GSH, 2-mercaptoethanol (βME), dithio-β(ME), 1,4-dithiothreitol (DTT), dithiane DTT, thiosulfate, dithionite, metabisulfite, sulfite, N-ethylmaleimide, cupic chloride or mycothiol.

The amount of recombinant proteins produced by a genetically modified host cell of the invention may be evaluated using standard methods known in the art. Such methods include, without limitation, Western blot analysis, SDS-polyacrylamide gel electrophoresis, non-denaturing gel electrophoresis, high performance liquid chromatography (HPLC) separation, immunoprecipitation, and/or activity assays such as DNA binding gel shift assays and alkaline phosphatase assay.

In some embodiments, the genetically modified host cell will secrete the recombinant protein into the medium. However, if the recombinant protein is not secreted from the host cells, it will be present in the cytoplasm and/or the nucleus (for eukaryotic host cells) or in the cytosol (for bacterial host cells). The host cells are typically disrupted mechanically or with a detergent to release the intracellular contents into a buffered solution. The recombinant protein is then purified or isolated from the culture medium or the cell lysate.

Alternatively, for recombinant proteins situated in the host cell cytoplasm and/or the nucleus (for eukaryotic host cells) or in the cytosol (for bacterial host cells), intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a recombinant protein has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The recombinant protein in its now soluble form can then be analyzed using gel electrophoresis, immunoprecipitation or the like. If it is desired to isolate the recombinant protein, isolation may be accomplished using standard methods such as those described herein and in Marston et al., *Meth. Enz.,* 182:264-275 (1990).

If inclusion bodies are not formed to a significant degree upon expression of a recombinant protein, then the protein will be found primarily in the supernatant after centrifugation of the cell homogenate. The protein may be further isolated or purified from the supernatant using methods such as those described herein.

The purification of recombinant protein from solution can be accomplished using a variety of techniques. If the polypeptide has been synthesized such that it contains a tag such as Hexahistidine (hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag.

For example, polyhistidine binds with great affinity and specificity to nickel, thus an affinity column of nickel (such as the Qiagen® nickel columns) can be used for purification of the polyHis tagged recombinant protein. See for example, Ausubel et al., eds., *Current Protocols in Molecular Biology,* Section 10.11.8, John Wiley & Sons, New York (1993). Additionally, the recombinant protein may be purified through the use of a monoclonal antibody which is capable of specifically recognizing and binding to the recombinant polypeptide.

Suitable procedures for purification thus include, without limitation, affinity chromatography, immunoaffinity chromatography, ion exchange chromatography, molecular sieve chromatography, High Performance Liquid Chromatography (HPLC), electrophoresis (including native gel electrophoresis) followed by gel elution, and preparative isoelectric focusing. In some cases, two or more purification techniques may be combined to achieve increased purity.

Methods of Improving Protein Folding of Recombinant Proteins

The invention provides for methods of improving protein folding of recombinant protein comprising growing a genetically modified host cell of the invention under conditions that permit expression of and improve proper folding of a disulfide bond containing protein. These methods may be carried out using the methods described above for recombinant protein production in general. The genetically modified host cells of the invention are capable of producing proteins that have improved protein folding due to the promotion of the formation of disulfide bonds.

In the method of improving folding of a recombinant protein, the host cell should be grown in media containing a redox-active compound, under conditions that permit expression of and improve yield of an active disulfide bond containing protein. Improvements in proper protein folding can be determined by detecting higher yields (e.g., higher mg active protein/liter of cell culture or higher activity of recombinant protein per liter of cell culture) of active recombinant disulfide bond containing protein. To test whether the conditions are improving the yield of active protein, the levels of recombinant active recombinant protein produced by modified host cells grown under the improved conditions may be compared to the levels of recombinant protein produced by unmodified host cells grown under normal or unmodified conditions. For example, at least about 2-fold, 3-fold, 4-fold, 5-fold, or higher yields of active recombinant protein is desired, this increase is relative to the yield from unmodified host cells in media that has not been supplemented with redox-active compounds. The active recombinant protein may be expressed µg/ml or mg/liter of active recombinant protein produced by the culture of modified host cells.

Methods for determining the extent of proper disulfide bond formation in the cytoplasm of a bacteria are standard in the art. In one exemplary method, the bacteria are transformed with a gene encoding a polypeptide (a "test" polypeptide) which normally contains at least one disulfide bond. Exemplary test polypeptides or proteins are those which are normally secreted from cells or which are membrane proteins. For use in the assays described herein, these polypeptides are modified by the deletion or mutation of the signal sequence, such that the proteins are not exported outside of the cytoplasm of the cell. The test may comprise expressing a complicated polypeptide, such as a protein having multiple disulfide bonds. In addition, the test polypeptide may lack biological activity when the disulfide bonds have not formed properly. Thus, when these proteins are expressed in the cytoplasm of wild type bacteria, no disulfide bonds are formed, and these proteins are not active.

Furthermore, the ability of a genetically modified host cell to produce disulfide bond containing proteins may be analyzed by determining the redox potential of the cytoplasm of the host cell. There are currently many different methods to measure cellular redox status, such as those as described in Gilbert et al. *Adv. Enzymol. Rel. Areas Mol. Biol.* 63:69, 1990; Holmgren and Fgestedt *J. Biol. Chem.* 257: 6926, 1982; and Hwang et al. *Science* 257: 1496, 1992.

To detect the physical properties of the recombinant protein produced by the genetically modified host cell of the invention, all polypeptides newly synthesized by the host cell can be labeled, e.g., with a radioisotope. Common radioisotopes that can be used to label polypeptides synthesized within a host cell include tritium ($^3$H), carbon-14 ($^{14}$C), sulfur-35 ($^{35}$S), and the like.

Improved protein folding may be characterized as a level that is at least two fold higher, at least 1 fold, at least 2 fold, at least 3 fold, at last 4 fold, at least 5 fold, at least 10 fold, at least 20 fold, at least 25 fold, at least 30 fold, at least 50 fold, 100 fold higher, or more fold higher relative to the production of properly folded protein in the wild type cell, unmodified or in a partially modified cell (i.e., a cell that has only some of the modifications, e.g., null mutations, or inserted genes).

EXAMPLES

Example 1

Inventory of Potentially Reductive TDORs in *B. subtilis*

As a first approach to increase the oxidative power of *B. subtilis* for more efficient secretion of disulfide bonds containing proteins, the potentially reductive systems of this organism were analyzed. It was hypothesized that the deletion of the corresponding genes or a reduction of their expression would make *B. subtilis* less reductive. In turn, this might improve the folding of proteins with disulfide bonds. For this purpose, three possible systems known from other organisms could be excluded a priori: first, *B. subtilis* lacks homologues of the enzymes that are required for the synthesis of glutathione in Gram-negative bacteria and eukarya; secondly, *B. subtilis* lacks the reducing agent mycothiol, that can be found in the cytoplasm of *Streptomyces* species and fungi (Newton et al., *J. Bacteriol.* 178:1990-1995, 1996); and thirdly, *B. subtilis* lacks the proteins involved in isomerisation pathways as found in *E. coli*.

Thioredoxin amino acid sequences of *B. subtilis* or *E. coli* were used for a BlastP search in the *B. subtilis* sequence database SubtiList [online database] (internet address: http (colon)//genolist(dot)pasteur(dot)fr/SubtiList) with the algorithms described by Altschul et al. (*Nucleic Acids Res.* 25:3389-3402, 1997). An arbitrary E. value lower than or equal to $10^{-3}$ was used to limit the number of sequences for further analyses. After a first run, using either *B. subtilis* TrxA or *E. coli* TrxA or TrxC as query sequences, the sequences found were used in turn as query sequences for a BlastP search in the SubtiList database. Multiple alignments were performed using ClustalX 1.81 (Thompson et al., *Nucleic Acids Res.* 25:4876-4882, 1996). Various protein weight matrices were used with pairwise and multiple alignment parameters. The best alignment, defined by the lowest score value, was obtained with the PAM350 matrix (Gap opening=10) for both pairwise (Gap extension=0.1) and multiple (Gap extension=0.2) alignment parameters. The presence of possible signal peptidase I cleavage sites was analyzed using the algorithms described by Nielsen et al. (*Int. J. Neural Syst.* 8:581-599, 1997). The presence of possible transmembrane segments was analyzed using the algorithms described by Krogh et al. (*J. Mol. Biol.* 305:567-580, 2001).

This focused the analysis on thioredoxins and thioredoxin-like proteins. BlastP searches revealed that the *B. subtilis* 168 genome encodes 12 thioredoxin(-like) proteins. These include four membrane proteins (BdbA, ResA, StoA/SpoIVH and YneN), and eight predicted cytoplasmic proteins, which are very similar to known thioredoxins and/or to ResA (Erlendsson et al., *J. Bacteriol* 186:6230-6238, 2004; Zhang et al., *J. Biol. Chem.* 281:8296-8304, 2006). FIG. 1 summarizes the amino acid sequence relationships between the thioredoxin-like proteins thus identified. The levels of sequence similarity between TrxA of *B. subtilis* (104 residues in total) and the TrxA-like proteins of *B. subtilis* ranged between 61% identical plus conserved residues in a stretch of 77 residues (YosR-TrxA) and 41% identical plus conserved residues in a stretch of 102 residues (StoA-TrxA).

Example 2

Cellular Levels of TrxA Determine the Level of PhoA Secretion

In order to test possible effects of the afore-mentioned potential TDORs on the secretion of a disulphide bond-containing protein, single trxA, ybdE, ydbP, ydfQ, ykuV, StoA (ykyV or spoIVH), yneN, ytpP and yusE mutants, and a strain that lacks the SPβ prophage carrying the bdbA and yosR genes, were transformed with plasmid pPSPhoA5.

Construction of the Mutants

DNA techniques were performed as described previously (Kouwen, *Mol. Microbiol.* 64:984-999, 2007). Mutant strains of potential cytoplasmic TDORs were constructed or obtained as follows. The *B. subtilis* 168 derivative strain ItrxA in which the essential (Scharf et a., *J. Bacteriol.* 180:1869-1877, 1998) trxA gene can be depleted was constructed previously (Smits et al., *J. Bacteriol.* 187:3921-3930, 2005). In the ItrxA strain, the trxA gene is placed under the control of the IPTG-inducible $P_{spac}$ promoter due to a single cross-over (Campbell-type) integration a pMutin2mcs vector in front of the trxA gene. When grown in the presence of 25 µM IPTG, $P_{spac}$ is active, but not fully induced. Strain ItrxA bdbC was obtained by transformation of the ItrxA strain with chromosomal DNA of a bdbC::Km$^r$ mutant and subsequent selection of IPTG-dependent and Km resistant transformants.

*B. subtilis* yusE was constructed as follows. A 1384-bp DNA fragment starting in the yusG gene and ending in the yusD gene was amplified using the primers gggaattcataagacagccgatgtggtc (SEQ ID NO:9) and gggggatccgtagaatagctcggcgaatg (SEQ ID NO:10), which contain EcoRI and BamHI restriction sites, respectively. The fragment was subsequently cleaved with EcoRI and BamHI, and ligated to EcoRI-BamHI-cleaved pUC18. The Sp-resistance cassette from plasmid pDG1727 was excised with BamHI and XhoII, and used to replace an internal BclI fragment of the pUC18-borne copy of yusE. The resulting plasmid pUSE-Spec was used to transform *B. subtilis* 168. As shown by PCR, the yusE gene of all Sp-resistant transformants tested (*B. subtilis* yusE) was disrupted with the Sp-resistance cassette of pUSE-Spec as a result of a double cross-over recombination event.

To construct *B. subtilis* ykuV, a 1516-bp DNA fragment starting in the ykuU gene and ending in the rok gene was amplified using the primers gggggatcccggcaaagtaagtcttgagg (SEQ ID NO:11) and ggggtcgacattgttctaaccgcaagcgc (SEQ ID NO:12), which contain BamHI and SalI restriction sites, respectively. The amplified fragment was cleaved with BamHI and SalI, and ligated to BamHI-SalI-cleaved pUC18. The Sp-resistance cassette from pDG1727 was excised using EcoRI and BsaWI, and used to replace an internal MunI-NgoMIV fragment of the pUC18-borne copy of ykuV. The resulting plasmid pKUV-Spec was used to transform *B. subtilis* 168. As shown by PCR, the ykuV gene of all Sp-resistant transformants tested (*B. subtilis* ykuV) was disrupted with the Sp-resistance cassette of pKUV-Spec as a result of a double cross-over recombination event.

*B. subtilis* ytpP was constructed as follows. A 1386-bp DNA fragment starting in the ytoP gene and ending in the ytpQ gene was amplified using the primers gggggtacccattgccgtgttccactgtt (SEQ ID NO:13) and gggctgcagggcaaccgtatcctctttga (SEQ ID NO:14), which contain KpnI and PstI restriction sites, respectively. The amplified fragment was cleaved with KpnI and PstI, and ligated to KpnI-PstI-cleaved pUC18. The Sp-resistance cassette from pDG1727 was excised with HincII and StuI and cloned in the unique BsaAI restriction site in the middle of the ytpP gene. The resulting plasmid pTPP-Spec was used to transform *B. subtilis* 168. As shown by PCR, the ytpP gene of all Sp-resistant transformants tested (*B. subtilis* ytpP) was disrupted with the Sp-resistance cassette of pTPP-Spec as a result of a double cross-over recombination event.

Single ybdE, ydbP, ydfQ, stoA (ykvV), yneN, and yusE mutants, and a strain that lacks the SPβ prophage carrying the bdbA and yosR genes, were either obtained from the BSFA or JAFAN strain collections (Kobayashi et al., *Proc. Natl. Acad. Sci. U.S.A* 100:4678-4683, 2003). The correct chromosomal integration of plasmids or antibiotic resistance markers was verified by PCR.

In order to overexpress the oxidative TDOR DsbA from *S. carnosus*, the pXTC expression system was used (Darmon et al., *Appl. Environ. Microbiol.* 72:6876-6885, 2006, Kouwen, *Mol. Microbiol.* 64:984-999, 2007). pXTC-ScdsbA, carrying dsbA of *S. carnosus* fused to the ribosome binding site and signal sequence of mntA of *B. subtilis* and under the transcriptional control of the xylA promoter ($P_{xylA}$), was constructed as follows. In a first PCR, a fragment of 92 bp containing the ribosomal binding site and signal sequence of mntA of *B. subtilis* was amplified using the primers pXTC_MntA_F (GGGGGACTAGTAAGAGGAG-GAGAAATATGAGACAA; SEQ ID NO:5) and pXTC_MntA_Scar_R (TTTTTGTGAGCATCCCGTTAAAGCAAAG-GTCGC; SEQ ID NO:6). A second PCR fragment of 566 bp resulted from amplifying the dsbA gene of *S. carnosus* using the primers pXTC_Scar_F (ttaacgggatgcTCACAAAAA-GACCCTGATTTA; SEQ ID NO:7) and pXTC_Scar_R (GGGGGGGATCCTTATTTTTCTAG-TAAATCTTTATATTCTT; SEQ ID NO:8). The resulting two PCR products had an overlap of twenty-one nucleotides. Using this overlap, the two different fragments could be fused in 10 PCR cycles without added primers. Next, the fused product was PCR-amplified with the primers pXTC_MntA_F and pXTC_Scar_R in 20 additional PCR cycles. The resulting product of 637 bp was cloned into pTOPO. After sequence verification, the fused dsbA gene was excised from this plasmid with BamHI and SpeI and ligated into the same restriction sites of plasmid pXTC, downstream of $P_{xylA}$, resulting in plasmid pXTC-ScdsbA.

Plasmid pXTC-ScdsbA was used to integrate the $P_{xylA}$ ScdsbA cassette together with the Tc resistance marker of pXTC (hereafter named XTC-ScdsbA cassette), into the amyE locus of *B. subtilis* 168 and *B. subtilis* ItrxA by double cross-over recombination. Selection for tetracycline resistance, and screening for an AmyE-negative phenotype on starch-containing plates enabled us to obtain strains *B. subtilis* X-ScdsbA and *B. subtilis* ItrxA X-ScdsbA, respectively.

Experimental Results

Plasmid pPSPhoA5 has a fusion between the pre-pro region of a lipase from *Staphylococcus hyicus* and the mature *E. coli* PhoA protein as described in Darmon et al (*Appl. Environ. Microbiol.* 72:6876-6885, 2006). *E. coli* PhoA is a sensitive reporter for TDOR activity in *B. subtilis*, because this protein contains two disulfide bonds and requires oxidative TDORs for folding into a protease-resistant conformation. Especially in the absence of BdbC and/or BdbD, the unfolded PhoA is readily degraded in the highly proteolytic environments of the *B. subtilis* cell wall and growth medium (Sarvas et al., *Biochim. Biophys. Acta* 1694:311-327, 2004). This basically provides an in vivo protease protection assay for probing the folding efficiency of secreted PhoA by oxidative TDOR activity. Interestingly, none of the strains lacking intact bdbA, ybdE, ydbP, ydfQ, ykuV, stoA, yneN, yosR, ytpP or yusE genes were significantly affected in the secretion of active PhoA of *E. coli*.

Unexpectedly, however, depletion of TrxA resulted in the secretion of PhoA at elevated levels. This was observed using a conditional trxA mutant strain (ItrxA) as described in Smits et al. (*J. Bacteriol.* 187:3921-3930, 2005), because TrxA is essential for the growth and viability of *B. subtilis* (Kobayashi et al., (*Proc. Natl. Acad. Sci. U.S. A.* 94:11857-11862, 1997, Scharf et al., *J. Bacteriol.* 180:1869-1877). In this strain, the trxA promoter region ($P_{trxA}$) was replaced with the IPTG-dependent $P_{spac}$ promoter. Growth of *B. subtilis* ItrxA on plates or in broth was strictly IPTG-dependent, unlike that of the parental strain 168. When cells of *B. subtilis* ItrxA were grown in LB broth, wild-type growth rates were observed at IPTG concentrations of 25 µM and higher.

Figure 2:
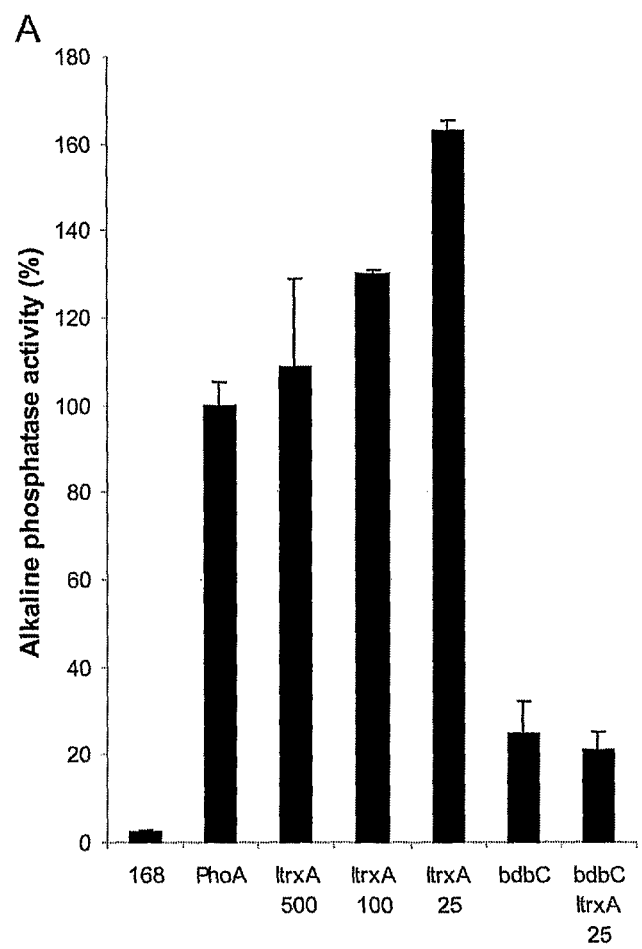
FIG. 2 depicts the BdbC-dependent secretion of PhoA by *B. subtilis* ItrxA measured by an alkaline phosphatase activity assay.

To investigate the importance of the cytoplasmic TrxA level on PhoA secretion, the ItrxA mutant strain transformed with plasmid pPSPhoA5 was further analyzed. The level of PhoA secretion into the growth medium was determined by alkaline phosphatase activity assays as described in Damon et al., (*Appl. Environ. Microbiol.* 72:6876-6885, 2006) and Western blotting. For this purpose, cells were grown in LB medium supplemented with 25, 100 or 500 µM IPTG. The results showed that, compared to the parental strain 168, the ItrxA strain secreted at least 1.5-fold more active PhoA when grown in the presence of 25 µM IPTG (FIG. 2). Under these conditions, cellular TrxA was barely detectable by Western blotting. The secretion of PhoA was similar to the levels observed in the parental strain when *B. subtilis* ItrxA was grown in the presence of 500 µM IPTG (FIG. 2), which coincided with wild-type levels of cellular TrxA. In contrast, PhoA secretion by the parental strain 168 was independent of the IPTG concentration in the growth medium, and the absence or presence of IPTG (25 µM to 500 µM) in the growth medium had no detectable influence on the TrxA levels in this strain. These observations indicated that, within the range of IPTG concentrations tested, the amount of active PhoA secreted by the ItrxA mutant is inversely proportional to the amount of TrxA in the cells.

Upon transformation with the plasmid pKTH10, which encodes the α-amylase AmyQ of *Bacillus amyloliquefaciens* which lacks disulfide bonds, the growth media of the ItrxA mutant (25 µM IPTG) and the parental strain 168 contained comparable amounts of AmyQ. The latter observation suggested that the improved PhoA secretion by the ItrxA mutant strain is not due to a generally improved synthesis or secretion of proteins, but rather to an improved post-translocational folding resulting in protease resistance of the mature PhoA protein. This view was confirmed by the observation that the extracellular proteome of the ItrxA mutant strain grown in the presence of 25 µM IPTG was indistinguishable from the extracellular proteome of the parental strain 168 (FIG. 2D).

The observed improvement of active PhoA secretion by the ItrxA mutant strain grown in the presence of 25 µM IPTG raised the question whether this increase still required the activity of BdbC. To answer this question, a pPSPhoA5-containing ItrxA bdbC double mutant strain was constructed. Importantly, this double mutant displayed IPTG-dependent growth, showing that the bdbC mutation did not suppress the ItrxA mutation. As shown in FIG. 2, PhoA secretion remained strongly BdbC-dependent, irrespective of the presence or absence of the ItrxA mutation. Furthermore, the secretion of PhoA by the ItrxA bdbC mutant did not vary when different amounts of IPTG were present in the growth medium. These findings suggest that the BdbCD thiol oxidation pathway is also required for PhoA folding under conditions of TrxA depletion.

Example 3

Cellular Levels of TrxA and BdbC Influence the Redox State of BdbD

To test whether the presence or absence of TrxA has an impact on the activity of the BdbCD thiol oxidation pathway, the redox state of BdbD was verified with the thiol-specific cross-linking reagent 4-acetamido-4'-maleimidyl-stilbene-2,2'-disulfonate (AMS; Molecular Probes) essentially as described by Kobayashi et al., (*Proc. Natl. Acad. Sci. U.S.A* 100:4678-4683, 2003). Due to the molecular mass of AMS, cross-linking of this reagent to reduced cysteine residues in a protein will cause a significant reduction of the mobility of this protein during SDS-PAGE (Kobayashi et al., *Proc. Natl. Acad. Sci. U.S.A* 100:4678-4683, 2003). BdbD contains only two cysteine residues, which are part of the CxxC active site. To study the redox state of BdbD, overnight cultures were used to prepare fresh lysates from the ItrxA strain (25 µM IPTG), the bdbC single mutant, the ItrxA bdbC double mutant, or the parental strain 168.

Cells were grown in LB medium and collected by centrifugation. The lysates were prepared either in the presence or absence of 15 mM AMS by resuspending the cell pellets in 25 mM Tris-HCl, 10 mM EDTA, 0.5 M glycerol, 0.25 mg/ml lysozyme (pH 8.0), and 15 mM AMS. After 30 minute incubation at 37° C., the samples were mixed with a loading buffer for SDS-PAGE that lacks reducing agents. Co-labeling during cell lysis was sufficient to distinguish between the different redox states of BdbD. Notably, AMS will only bind covalently to free thiol groups in reduced BdbD molecules. Upon boiling of the samples for 7 minutes, BdbD molecules with or without bound AMS were separated by non-reducing SDS-PAGE. Finally, the different BdbD species were visualized by Western blotting and immunodetection with specific polyclonal antibodies. The relative amounts of BdbD species with or without bound AMS was determined using the ChemiGenius $XE^2$ Bio-Imaging system and the GeneTools Analysis Software package (Synoptics). All experiments were repeated at least four times.

Somewhat less than 50% of the BdbD molecules of the parental strain 168 were labeled with AMS. By contrast, significantly less BdbD molecules were AMS labeled in the ItrxA strain whereas significantly more BdbD molecules were AMS-labeled in the bdbC or ItrxA bdbC mutant strains. Remarkably, these relative differences appeared even more pronounced in exponentially growing cells of *B. subtilis* 168, ItrxA and bdbC. These observations indicate that significantly more BdbD molecules were oxidized in the ItrxA strain than in the parental strain and, conversely, that the bdbC mutation resulted in lowered numbers of oxidized BdbD molecules. Furthermore, the control experiments with lysates of the strains prepared in the absence of AMS showed that BdbD migrated as a single band. Together, these findings indicated that the cytoplasmic TrxA levels affected the redox state of BdbD in a BdbC-dependent manner.

Example 4

Expression of DsbA Increases PhoA Secretion

An alternative potential approach to increase the capacity of *B. subtilis* for thiol oxidation is to induce the overproduction of known thiol oxidases. However, attempts to increase the levels of BdbC and BdbD have not been successful to date. Therefore, the possibility of expressing heterologous oxidases was investigated.

Previous studies have demonstrated that the major oxidase DsbA of *Staphylococcus aureus* (here referred to as SaDsbA), which is a homologue of *B. subtilis* BdbD, was able to complement for the loss of both BdbC and BdbD in the secretion of active PhoA (Kouwen et al., *Mol. Microbiol.* 64:984-999, 2007). Moreover, when SaDsbA was expressed in the parental strain 168, an increase in *E. coli* PhoA secretion of about 1.5-2.0 fold was observed, similar to the above increase observed upon TrxA depletion (see Example 2).

However, since *S. aureus* is known as a dangerous pathogen Massey et al., *Nat. Rev. Microbiol.* 4:953-958, 2006; Sibbald et al., *Microbiol. Mol. Biol. Rev.* 70:755-788, 2006), the application potential of SaDsbA for biotechnological purposes is limited. For this reason, a search for a DsbA protein from a non-pathogenic close relative of *S. aureus* was conducted. A good best source for a dsbA gene was *Staphylococcus carnosus*, which is widely used as a starter in the fermentation of cheese and dry-sausage. Accordingly, this organism has the Generally Recognized As Safe (GRAS) status. *B. subtilis* strains containing genes that originated from this staphylococcal species should therefore be more generally accepted for industrial applications.

An *S. carnosus* homologue of *S. aureus* DsbA (referred to herein as "ScDsbA" SEQ ID NO:4) was identified by BlastP searches (51% identical amino acids) in the sequenced genome of *S. carnosus* strain TM300. Like SaDsbA, the ScDsbA protein was homologous to *B. subtilis* BdbD (36% identical amino acids). In order to express the ScDsbA in *B. subtilis*, the xylose inducible pXTC expression system was used as to express the *S. aureus* SaDsbA described in Kouwen et al., (*Mol. Microbiol.* 64:984-999, 2007). For this purpose, the sequence encoding the mature ScDsbA lipoprotein was fused to the ribosomal binding site and signal sequence of the *B. subtilis* mntA gene, which codes for an abundantly expressed lipoprotein of this organism (Antelmann et al., *Genome Res.* 11:1484-1502, 2001). Upon integration of the XTC-ScdsbA cassette containing this hybrid ScdsbA gene into the *B. subtilis* 168 chromosome, xylose-inducible expression of cell-associated ScDsbA was obtained (strains containing this cassette are now referred to as X-ScdsbA).

Antibodies directed against SaDsbA were used for the immunodetection of ScDsbA. These antibodies were cross-reactive with ScDsbA. As expected, the cellular levels of ScDsbA depended on the amount of xylose added to the growth medium. The largest levels of cellular ScDsbA were observed when the X-ScdsbA cells were induced with 1.0% xylose or more, whereas no ScDsbA was detectable when cells were grown in the absence of xylose.

Figure 3:
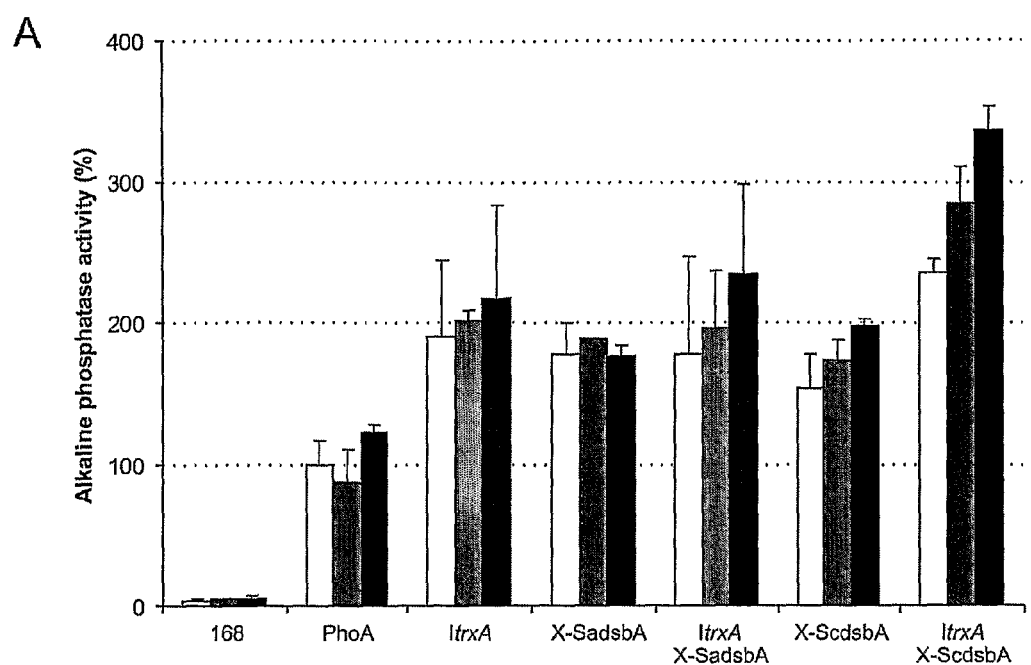
FIG. 3 depicts increased production of *E. coli* PhoA by engineered *B. subtilis* strains as measured by an alkaline phosphatase activity assay. The *B. subtilis* ItrxA, X-SadsbA, ItrxA X-SadsbA, X-ScdsbA and ItrxA X-SadsbA strains or the parental strain 168 (PhoA) were transformed with pPSPhoA5 for *E. coli* PhoA production. All strains and the parental strain 168 (168) were grown overnight in LB medium containing 0.5% xylose (white bars) and an additional 100 mg/ml cystine (grey bars) or cysteine (black bars).

In order to assess the effect of ScDsbA expression on the extracellular accumulation of active *E. coli* PhoA, *B. subtilis* strain X-ScdsbA was transformed with plasmid pPSPhoA5. For comparison, the PhoA production by strain X-SadsbA, ItrxA (25 µM IPTG) and the combined strains X-ScdsbA ItrxA and X-ScdsbA ItrxA, all of which were transformed with plasmid pPSPhoA5, were assayed in parallel. The results indicated that expression of ScDsbA led to increased secretion of active PhoA (FIG. 3, white bars) compared to the parental strain. The extent to which ScDsbA expression increased the level of extracellular PhoA was comparable to that upon expression of SaDsbA, indicating that these proteins are functionally exchangeable when expressed in *B. subtilis*. Furthermore, the expression of ScDsbA or SaDsbA, and the depletion of TrxA resulted in a comparable increase in the extracellular PhoA levels of about 1.5-2.0 fold. Remarkably, when TrxA depletion was combined with ScDsbA or SaDsbA expression, even higher levels of active extracellular PhoA were achieved, especially in the combined X-ScdsbA ItrxA strain (FIG. 5A, white bars).

The levels of PhoA activity in the different growth medium samples correlated well with the levels of mature PhoA protein detected in the respective samples, as shown by Western blotting. Compared to the parental strain expressing PhoA, significantly less extracellular breakdown products of PhoA were observed in all mutant strains tested. The lowest amounts of PhoA degradation products were observed in ItrxA strains depleted of TrxA. Furthermore, unprocessed forms of the pro-PhoA protein in the strains containing the ItrxA mutation were visible, and to a lesser extent, this was also the case for X-SadsbA and X-ScdsbA strains. The highest amounts of PhoA protein were observed in medium fractions of the X-ScdsbA ItrxA strain that was depleted of TrxA. Taken together, these results demonstrated that modulation of cytoplasmic TrxA and/or extracytoplasmic TDOR levels result in increased levels of secreted active PhoA.

Example 5

Optimized Levels of Secreted PhoA Facilitated by Redox-Active Medium Compounds

It has been reported that the activity of staphylococcal DsbA promoting the extracellular accumulation of *E. coli* PhoA depends on redox-active compounds in the growth medium. This was shown by growing DsbA producing *B. subtilis* in synthetic media with or without cysteine/cystine (Kouwen et al., *Mol. Microbiol.* 64:984-999, 2007). Therefore, whether this DsbA activity could be enhanced by addition of excess redox-active compounds, such as cysteine or cystine, when cells were grown in the rich LB medium was investigated. For this purpose, all TrxA depletion and/or DsbA-expressing strains were grown, in parallel cultures, in the presence of 100 µg/ml added cystine (i.e. oxidized cysteine) or cysteine. Addition of either cystine or cysteine to the ItrxA X-ScdsbA strain resulted in strongly increased levels of extracellular accumulated PhoA. This increase was most pronounced when cysteine was added. Furthermore, this positive trend was also observed for X-ScdsbA strain, but the degree of stimulation was lower than in the ItrxA X-ScdsbA strain. For the other strains the addition of cysteine or cystine to the growth medium did not result in statistically significant increased extracellular PhoA levels. The PhoA activity data were confirmed by Western blotting, showing that all observed increases in activity correlated with increased PhoA protein levels. Especially, the addition of cysteine resulted in a reduced accumulation of PhoA degradation products, even in the parental strain 168.

To investigate whether cystine or cysteine in the growth medium would affect known TDORs that influence secretion of active PhoA, the cellular levels of DsbA, BdbD and TrxA were investigated. The levels for these proteins were not affected by the presence or absence of added cystine or cysteine.

The observation that addition of cysteine or cystine to the medium of strains expressing *S. carnosus* DsbA leads to increased extracellular levels of active PhoA is in agreement with the recently documented cysteine-dependency of *S. aureus* DsbA for activity (Kouwen et al., *Mol. Microbiol.* 64:984-999, 2007). Most likely, this relates to the fact that all (sequenced) staphylococci lack BdbC-like quinone reductases for DsbA reoxidation during catalysis (Kouwen et al., *Mol. Microbiol.* 64:984-999, 2007). This requirement for redox-active medium components for DsbA activity is not obvious when cells are grown in LB medium, because this growth medium already contains such components. However, our present findings with *S. carnosus* DsbA, indicate that redox-active components are present in limiting amounts for optimal activity of this thiol oxidase. It should be noted that both the addition of cysteine or cystine to the media had similar effects. Most likely, this is due to the fact that cysteine is readily oxidized to cystine in the presence of molecular oxygen. In fact, addition of cysteine seems to be more effective than addition of cystine itself, which can be explained by the poor solubility of cystine. Furthermore, recent studies by Smits et al. (*J. Bacteriol.* 187:3921-3930, 2005) suggest that TrxA-depleted cells are auxotrophic for cysteine, since genes for cysteine synthesis and uptake are expressed at significantly elevated levels and growth inhibition of severely TrxA-depleted cells could be reverted by adding cysteine to the growth medium. Under these conditions cysteine may actually serve to protect various cytoplasmic proteins against irreversible thiol oxidation (Hochgrafe et al., *J. Biol. Chem.* 282:25981-25985, 2007, Lee et al., *Proc. Natl. Acad. Sci. U.S.A* 104:8743-8748, 2007). Addition of cysteine is therefore preferred over cystine in order to increase the oxidative potential of the strains expressing *S. carnosus* DsbA.

SEQUENCE LISTING

The sequence listing submitted via EFS on May 20, 2011, in compliance with 37 C.F.R. §1.52(e), is incorporated herein by reference. The sequence listing text file submitted via EFS contains the file "31116WO-seqlist.txt", created on May 20, 2011, which is 6,244 bytes in size.

What is claimed:

1. A genetically modified *Bacillus* host cell comprising i) a genetic modification to functionally delete or inactivate the gene encoding endogenous thioredoxin A (TrxA) polypeptide in the host cell, and ii) a nucleic acid sequence encoding a heterologous *Staphylococcus carnosus* disulfide bond A (DsbA) polypeptide, wherein the heterologous *Staphylococcus carnosus* DsbA polypeptide comprises an amino acid sequence that is at least 95% identical to the amino acid sequence of SEQ ID NO:4 and has a thiol oxidase activity.

2. The genetically modified *Bacillus* host cell of claim 1, wherein the endogenous TrxA polypeptide comprises the amino acid sequence of SEQ ID NO:2, and the heterologous *Staphylococcus carnosus* DsbA polypeptide comprises the amino acid sequence of SEQ ID NO:4.

3. The genetically modified *Bacillus* host cell of claim 1 further comprising a nucleic acid sequence encoding a disulfide bond containing protein.

4. A culture of the host cells of claim 1.

5. The culture of claim 4, wherein the culture is grown in a medium containing a redox-active compound.

6. The culture of claim 5, wherein the redox-active compound is selected from the group consisting of: cysteine, cystine, glutathione, 2-mercaptoethanol (BME), 1,4-dithiothreitol (DTT), thiosulfate, dithionite, metabisulfite, sulfite, N-ethylmaleimide and mycothiol.

7. A method of producing a disulfide bond containing protein in a *Bacillus* host cell comprising i) functionally deleting or inactivating the gene encoding endogenous TrxA polypeptide in the host cell, ii) introducing a nucleic acid sequence encoding a heterologous *Staphylococcus carnosus* DsbA polypeptide in the host cell, wherein the heterologous *Staphylococcus carnosus* DsbA polypeptide comprises an amino acid sequence that is at least 95% identical to the amino acid sequence of SEQ ID NO:4 and has a thiol oxidase activity, and iii) growing the host cell in media containing a redox-active compound, wherein the host cell produces the disulfide bond containing protein and secretes the protein into the media.

8. The method of claim 7, wherein the TrxA polypeptide is selected from the group consisting of i) an amino acid sequence of SEQ ID NO:2, ii) an amino acid sequence encoded by the nucleic acid sequence of SEQ ID NO:1, iii) an amino acid sequence that is at least 90% identical to the amino acid sequence of SEQ ID NO:2, iv) an amino acid sequence encoded by a nucleic acid sequence that is at least 90% identical to the nucleic acid sequence of SEQ ID NO:1, and v) an amino acid sequence encoded by a nucleic acid sequence that hybridizes under stringent conditions to the complement of SEQ ID NO:1.

9. The method of claim 7, wherein the *Staphylococcus carnosus* DsbA polypeptide is introduced by transforming the host cell with a plasmid comprising a nucleic acid sequence encoding the *Staphylococcus carnosus* DsbA polypeptide.

10. The method of claim 7, wherein the DsbA polypeptide comprises the amino acid sequence of SEQ ID NO:4.

11. The method of claim 7, wherein the host cell is *Bacillus subtilis*.

12. The method of claim 7, wherein the functionally deleting or inactivating the gene encoding the endogenous TrxA polypeptide comprises mutating the gene encoding the endogenous TrxA polypeptide.

13. The method of claim 12, wherein the mutation is a deletion mutation, substitution mutation or insertion mutation.

14. The method of claim 7, wherein the redox-active compound is selected from the group consisting of cysteine, cystine, glutathione, 2-mercaptoethanol (BME), 1,4-dithiothreitol (DTT), thiosulfate, dithionite, metabisulfite, sulfite, N-ethylmaleimide or mycothiol.

15. The method of claim 7, wherein the cytoplasmic reductase is a TrxA polypeptide comprising the amino acid sequence of SEQ ID NO:2; the oxidase is a DsbA polypeptide comprising the amino acid sequence of SEQ ID NO:4.

16. A method of improving protein folding of a recombinant disulfide bond containing protein comprising a) growing a genetically modified *Bacillus* host cell in media containing a redox-active compound, under conditions that permit expression of and improve proper folding of a disulfide bond containing protein, wherein said host cell (i) comprises a genetic modification to functionally delete or inactivate the gene encoding endogenous thioredoxin A (TrxA) polypeptide in the host cell, (ii) comprises a nucleic acid sequence encoding a heterologous *Staphylococcus carnosus* disulfide bond A (DsbA) polypeptide, wherein the heterologous *Staphylococcus carnosus* DsbA polypeptide comprises an amino acid sequence that is at least 95% identical to the amino acid sequence of SEQ ID NO:4 and has a thiol oxidase activity, and (iii) secretes a heterologous disulfide bond containing protein; and b) optionally, isolating said secreted protein from the media.

* * * * *